(12) United States Patent
Kobayashi et al.

(10) Patent No.: US 8,065,945 B2
(45) Date of Patent: Nov. 29, 2011

(54) TISSUE CUTTING DEVICE, TISSUE CUT ASSISTING DEVICE AND ACCOMMODATION HOUSING

(75) Inventors: Hironori Kobayashi, Ono (JP); Masahiko Tsujimoto, Takatsuki (JP); Michihiko Noguchi, Wakayama (JP); Koichi Yamagata, Kobe (JP); Yasunori Maekawa, Kobe (JP)

(73) Assignee: Sysmex Corporation, Kobe (JP)

( * ) Notice: Subject to any disclaimer, the term of this patent is extended or adjusted under 35 U.S.C. 154(b) by 1220 days.

(21) Appl. No.: 11/262,098

(22) Filed: Oct. 28, 2005

(65) Prior Publication Data
US 2006/0106378 A1  May 18, 2006

(30) Foreign Application Priority Data

Oct. 29, 2004 (JP) .................. 2004-316374

(51) Int. Cl.
*G01N 1/06* (2006.01)
(52) U.S. Cl. ............. 83/915.5; 30/173; 30/304; 30/329; 30/339
(58) Field of Classification Search .......... 30/173, 30/182, 304, 329, 335, 337, 2, 40.2, 50, 51, 30/172, 338, 336, 339; 83/915.5
See application file for complete search history.

(56) References Cited

U.S. PATENT DOCUMENTS

| 2,396,443 | A | * | 3/1946 | Singer | 30/304 |
|---|---|---|---|---|---|
| 2,709,298 | A | * | 5/1955 | Mater | 30/117 |
| 4,085,504 | A | * | 4/1978 | Nagy | 30/123 |
| 4,391,043 | A | * | 7/1983 | Sizemore et al. | 30/330 |
| 4,408,396 | A | * | 10/1983 | Scholl | 30/294 |
| 4,578,865 | A | * | 4/1986 | Keller | 30/304 |
| 4,719,701 | A | * | 1/1988 | Williams | 30/304 |
| 5,507,765 | A | | 4/1996 | Mott | |
| 6,230,051 | B1 | | 5/2001 | Cormier et al. | |
| 6,311,400 | B1 | * | 11/2001 | Hawes et al. | 30/527 |
| 6,434,828 | B1 | * | 8/2002 | Andrews | 30/50 |
| 7,040,022 | B2 | * | 5/2006 | Ping | 30/161 |

FOREIGN PATENT DOCUMENTS

| GB | 2404607 A | 2/2005 |
|---|---|---|
| JP | 58-184646 | 12/1983 |
| JP | 04-064753 | 6/1992 |
| JP | 07-218398 | 8/1995 |
| JP | 2004-257855 A | 9/2004 |
| JP | 2005-098702 | 4/2005 |

* cited by examiner

*Primary Examiner* — Edward Landrum
(74) *Attorney, Agent, or Firm* — Brinks Hofer Gilson & Lione

(57) ABSTRACT

A tissue cutting device is described, a representative one of which includes: a handle part; a head unit including comprising a plurality of blades arranged so as to extend substantially parallel with a longitudinal direction of the handle part at intervals and a blade holding portion for holding the plurality of blades; and a head holding part located at the distal end of the handle part, for holding the head.

12 Claims, 21 Drawing Sheets

TISSUE CUTTING DEVICE, TISSUE CUT ASSISTING DEVICE AND ACCOMMODATION HOUSING

This application claims priority under 35 U.S.C. §119 to Japanese Patent Application No. 2004-316374 filed Oct. 29, 2004, the entire content of which is hereby incorporated by reference.

FIELD OF THE INVENTION

The present invention relates to tissue cutting devices, tissue cut assisting devices and accommodation housings, more particularly, to a tissue cutting device for cutting a biological tissue, a tissue cut assisting device for assisting cutting of a biological tissue using the tissue cutting device, and an accommodation housing for accommodating a head unit of the tissue cutting device.

BACKGROUND

In a conventional surgery of breast cancer, dissection of axillary lymph nodes (biological tissue) is commonly performed. By such dissection of axillary lymph nodes, it is possible to prevent occurrence of a problem that gradually hardened and enlarged lymph nodes where cancer metastasis occurs cause disorders in critical areas such as nerves and blood vessels. Additionally, by conducting dissection of axillary lymph nodes, it is possible to know whether metastasis of breast cancer to lymph nodes occurs, and hence it is possible to predict systemic metastasis from the breast cancer. This also allows determination of postoperative regimen (choice of anticancer agent, need of radiation therapy).

As a technique of dissection of lymph nodes, a method called "sentinel lymph node biopsy" is conventionally known. The "sentinel lymph node biopsy" involves finding a sentinel lymph node during a surgery of breast cancer, removing it, preparing a histological specimen of the sentinel lymph node and conducting a rapid histological examination. The term "sentinel lymph node" used herein means a node, which a cancerous cell entering a lymph duct from a source lesion of the cancer reaches first. When cancer spreads to lymph nodes, metastasis to sentinel lymph nodes unexceptionally occurs. Therefore, by conducting a sentinel lymph node biopsy as described above, it is possible to determine the presence of metastasis of breast cancer to other lymph nodes. That is, when breast cancer does not spread to sentinel lymph nodes, dissection of the remaining lymph nodes is no longer necessary, whereas when breast cancer spreads to sentinel lymph nodes, dissection of a plurality of lymph nodes around the lesion is required depending on the situation. By conducting a sentinel lymph node biopsy in a manner as described above, it is possible to avoid unnecessary dissection of lymph nodes, and hence it is possible to reduce the burden on a patient.

In an exemplary procedure of the above conventional lymph node rapid histological examination in a surgery, first, a removed lymph node of elliptical spherical shape is longitudinally split in such a way that the split face becomes largest. After freezing the sections of the split lymph node, the split section is sliced into a thickness of several microns using a microtome. Then the slice of lymph node is stained with H-E (hematozylin eosin), and the stained lymph node is observed under a microscope, thereby accomplishing a rapid histological examination of lymph node. In conducting the rapid histological examination by splitting a removed lymph node into two pieces, if there is no cancerous cell in the split section of the lymph node, it could be recognized as negative regardless of presence of a trace of cancerous cell in the lymph node. For this reason, in order to decrease the probability of false recognition as "negative" regardless of presence of a trace of cancerous cell in a lymph node, conventionally, a lymph node is longitudinally split into three or more sections so as to obtain the largest split section in the splitting step of lymph node in the rapid histological examination.

Conventionally, in a step of longitudinally splitting a lymph node into three or more sections so as to obtain the largest split section in the splitting step of lymph node in the rapid histological examination, a cutting device having only one blade such as replaceable blade for microtome, razor blade or trimming knife handle adopting a replaceable blade (product of FEATHER Safety Razor Co., Ltd.) is used. One exemplary cutting device having only one blade is a pathologic trimming holder (see for example, Japanese Patent Application Laid-Open (JP-A) No. 2004-257855).

However, when the aforementioned conventional cutting device having only one blade is used in the splitting step of lymph node in the rapid pathologic assay, in order to split a lymph node into three or more sections along the longitudinal direction of the lymph node so as to obtain the largest split surface, it is necessary to repeat a cutting operation with a cutting device twice or more times. This causes a drawback that the shape of the lymph node is lost during the first operation because a lymph node is fragile and so small that the transverse length falls within the range of several millimeters to several tens millimeters. As a result, the second and later cutting operations of lymph node (biological tissue) become difficult, posing a problem that efficiency of cutting operation by which a lymph node (biological tissue) is split into three or more sections is deteriorated.

SUMMARY

The present invention was devised to solve the problems as described above, and one object of the present invention is to provide a tissue cutting device capable of improving the efficiency of a cutting operation by which a biological tissue is split into three or more sections.

Another object of the present invention is to provide a tissue cut assisting device capable of improving the efficiency of cutting operation for splitting a biological tissue into a plurality of sections.

A further object of the present invention is to provide an accommodation housing capable of accommodating a head unit while preventing foreign matters from adhering to a blade.

A tissue cutting device according to the first aspect of the present invention is intended for cutting a biological tissue into sections of a predetermined thickness, and the issue cutting device comprises: a handle part; a head unit including comprising a plurality of blades arranged so as to extend substantially parallel with a longitudinal direction of the handle part at intervals and a blade holding portion for holding the plurality of blades; and a head holding part located at the distal end of the handle part, for holding the head unit.

A tissue cut assisting device according to the second aspect of the present invention is intended for assisting cutting of a biological tissue using a tissue cutting device for cutting a biological tissue, and the tissue cut assisting device comprises: a base; a pair of guiding members disposed on the base, for guiding a cutting operation of the biological tissue using the tissue cutting device; a mounting member mounted on a predetermined position between the pair of guiding members, for placement of the biological tissue.

An accommodation housing according to the third aspect of the present invention is intended for accommodating a head unit of a tissue cutting device for cutting a biological tissue, the tissue cutting device including a handle part, a head unit including a plurality of blades arranged so as to extend substantially parallel with a longitudinal direction of the handle part at intervals and a blade holding portion for holding the plurality of blades and a head holding part disposed at the distal end of the handle part for holding the head unit, and the accommodation housing comprises: a head unit receiving portion for receiving the blades of the head unit so as to face a bottom part but not to contact with an inner face of a bottom part.

DETAILED DESCRIPTION OF THE PREFERRED EMBODIMENT

Embodiments of the present invention will be described below with reference to attached drawings.

Figure 1:
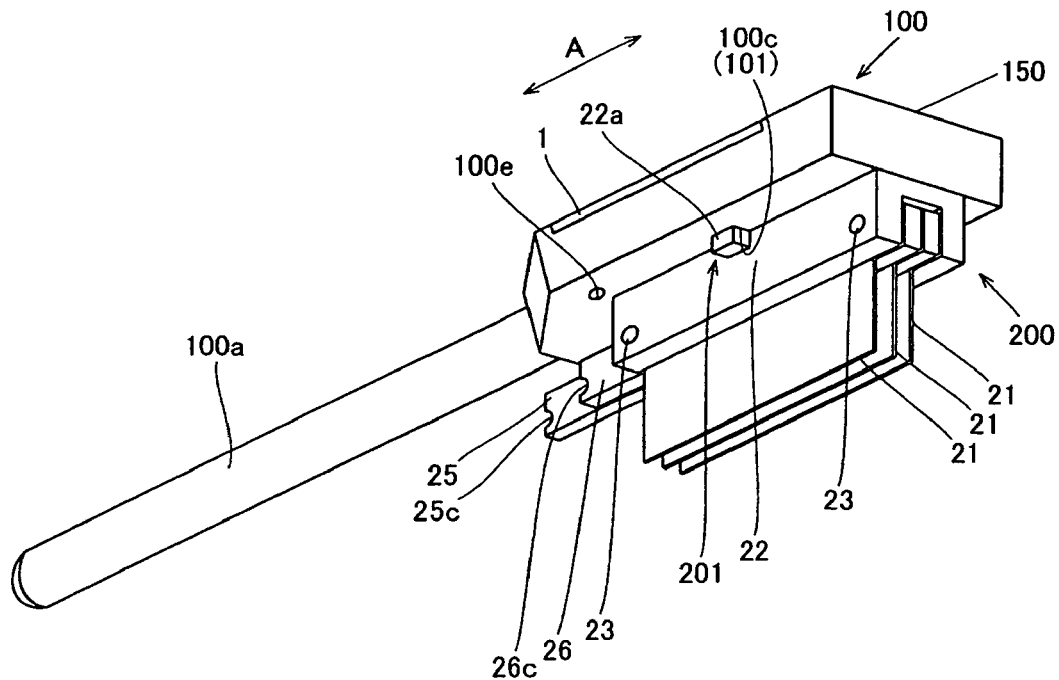
[FIG. 1] A perspective view of a structure of a tissue cutting device according to one embodiment of the present invention.
Figure 2:
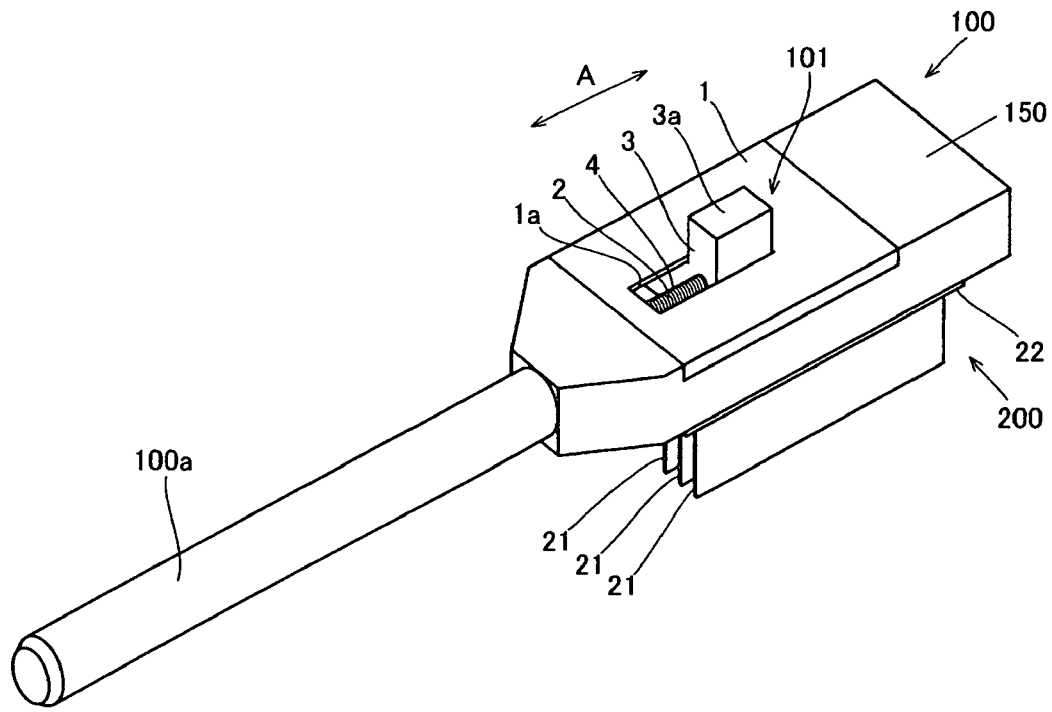
[FIG. 2] A perspective view of a structure of a tissue cutting device according to one embodiment of the present invention.
Figure 3:
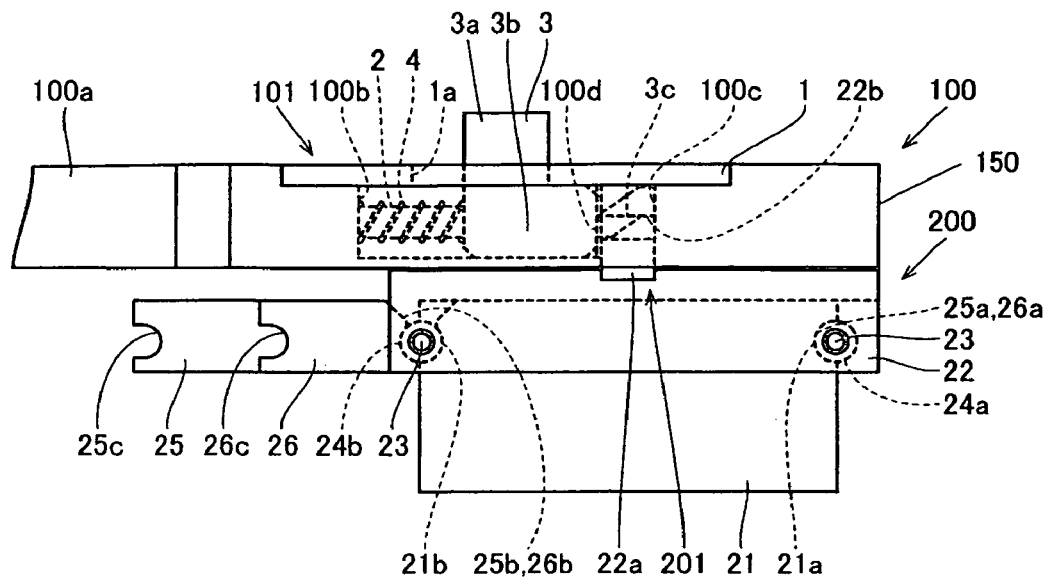
[FIG. 3] An enlarged view around a distal end of the tissue cutting device according to one embodiment shown in FIGS. 1 and 2.
Figure 4:
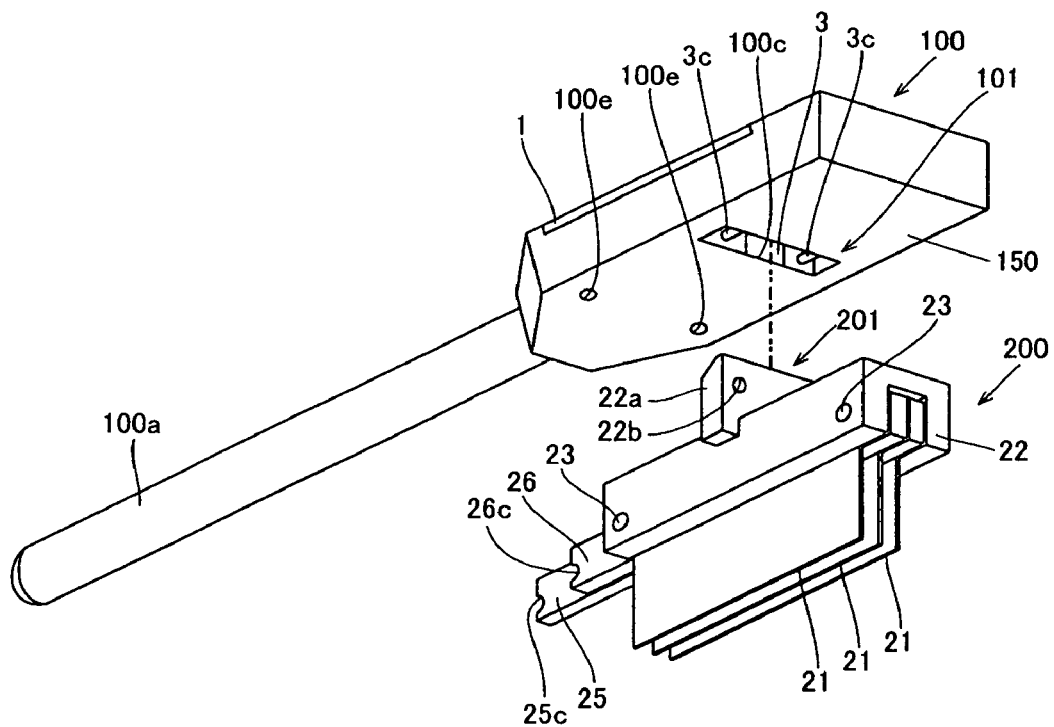
[FIG. 4] A perspective view showing a state in which a head is removed from a holder of the tissue cutting device according to one embodiment shown in FIGS. 1 and 2.

FIGS. 1 and 2 are perspective views showing a structure of a tissue cutting device according to one embodiment of the present invention. FIG. 3 is a enlarged view around the distal end of the tissue cutting device according to one embodiment shown in FIGS. 1 and 2, FIG. 4 is a perspective view showing the state that a head unit is removed from a holder unit of the tissue cutting device according to one embodiment shown in FIGS. 1 and 2. FIGS. 5 to 8 are detail drawings for illustrating a structure of a holder unit of the tissue cutting device according to one embodiment shown in FIGS. 1 and 2, and FIGS. 9 to 17 are detail views for illustrating a structure of a head unit of the tissue cutting device according to one embodiment shown in FIGS. 1 and 2. First, referring to FIGS. 1 to 4, explanation will be made on the overall structure of the tissue cutting device for cutting a biological tissue according to the present embodiment.

As shown in FIGS. 1 to 4, a tissue cutting device of the present embodiment includes a holder unit 100 including a handle 100a and a holding part 150, and a head unit 200 attached to the holding part 150 on opposite side (distal end side) of the handle 100a of the holder unit 100.

In the present embodiment, as shown in FIGS. 1 and 2, the head unit 200 includes three blades 21 arranged so as to be parallel with a longitudinal direction (A direction) of the holder unit 100 while keeping about 2 mm interval there between, and a blade holding portion 22 for holding the three blades 21. As shown in FIGS. 3 and 4, the holder unit 100 and the head unit 200 are respectively provided with attachment/detachment mechanism portions 101 and 201 so as to allow the head unit 200 to be attached/detached to/from the holding part 150 of the holder unit 100.

Figure 5:
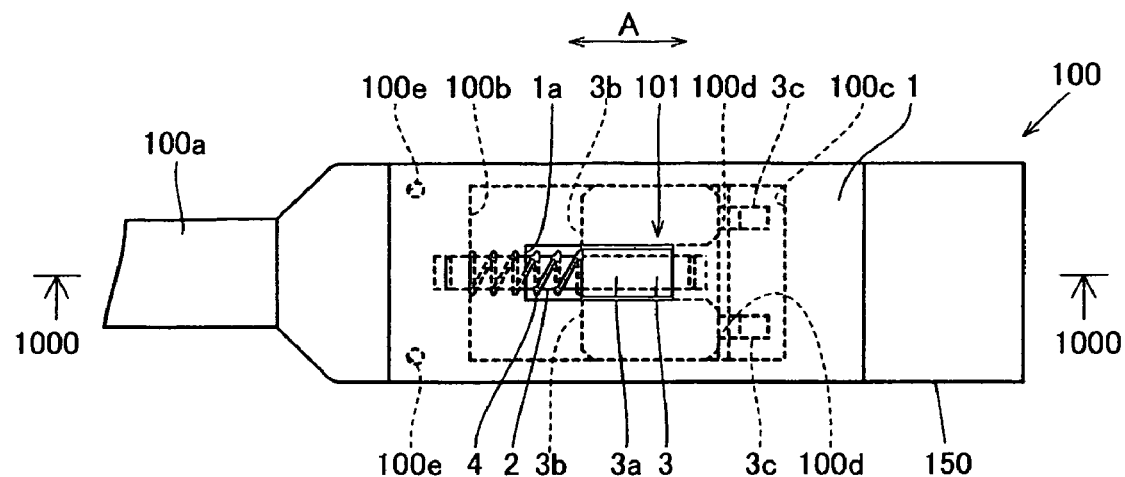
[FIG. 5] A plan view of a holder unit of the tissue cutting device according to one embodiment shown in FIGS. 1 and 2, viewed from above.
Figure 6:
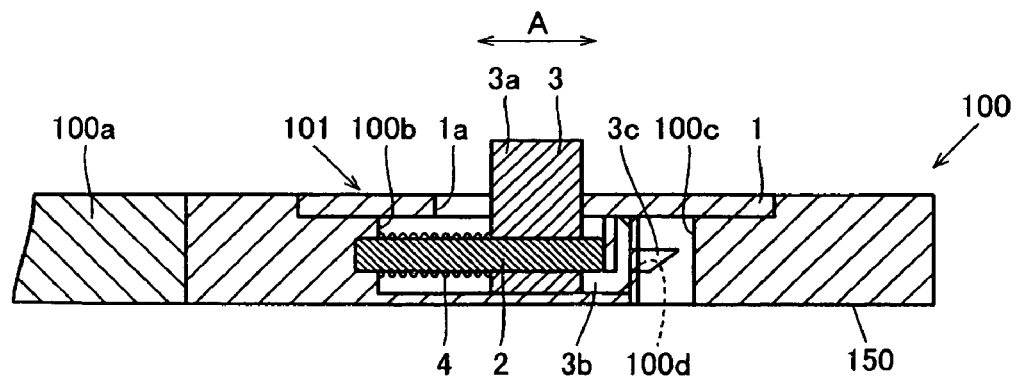
[FIG. 6] A sectional view seen along the line 1000-1000 in FIG. 5.
Figure 7:
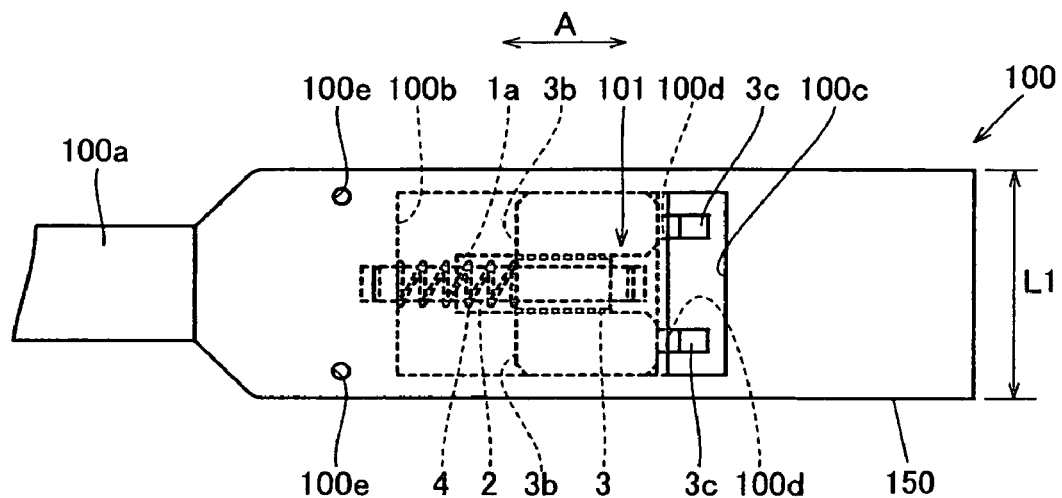
[FIG. 7] A plan view of a holder unit of the tissue cutting device according to one embodiment shown in FIGS. 1 and 2, viewed from below.

Referring now to FIGS. 5 to 8, a concrete structure of the holder unit 100 of the present embodiment will be explained described. As shown in FIGS. 5 to 7, the holding part 150 provided on the distal end side of the holder unit 100 of the present invention is formed with a recess 100b having a bottom part on its bottom side, and a hole 100c disposed to contact the recess 100b. These recess 100b and hole 100c are coupled via two coupling holes 100d. Also as shown in FIGS. 5 to 7, on the distal end side of the holder unit 100 is provided two water discharge holes 100e connected with the recess 10b.

Figure 8:
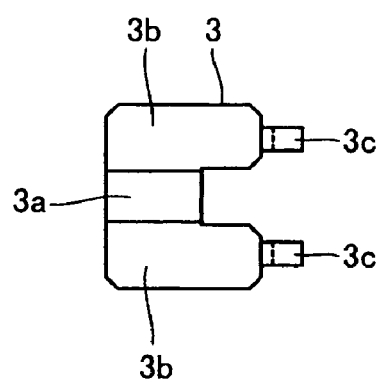
[FIG. 8] A plan view of a movable member of a holder unit of the tissue cutting device according to one embodiment shown in FIGS. 1 and 2.

As shown in FIGS. 5 and 6, on an upper part of the holding part 150 an upper cover 1 is attached so as to cover the recess 100b and the hole 100c. The upper cover 1 is formed with an opening 1a on a predetermined position corresponding to the recess 100b. Inside the recess 100b is attached a shaft 2. To the shaft 2 is attached a movable member 3 so as to be movable in the longitudinal direction (A direction of the holder unit 100) along the shaft 2. As shown in FIGS. 6 and 8, the movable member 3 has a lever 3a disposed to project from the top face of the upper cover 1, a pair of coupler supporting portions 3b disposed to sandwich the lever 3a, and a pair of couplers 3c disposed in distal end parts of the pair of coupler supporting portions 3b. The pair of couplers 3c have a tapered shape inclined at a certain angle. The couplers 3c are disposed to project inside the holes 100c via the coupling holes 10d. As shown in FIGS. 5 and 6, to the shaft 2 a compression spring 4 for biasing the movable member 3 toward the holes 100c is attached. The aforementioned attachment/detachment mechanism portion 101 is made of the recess 100b, the holes 100c, the upper cover 1, the shaft 2, the movable member 3, and the compression spring 4.

Next, referring FIGS. 3 and 6, and FIGS. 9 to 17, a concrete structure of the head unit 200 according to the present embodiment will be described explained. As shown in FIG. 11, the blade holding portion 22 of the head unit 200 of the present embodiment is formed into a square U shape, and disposed so that its open end faces downwardly. In an upper part on the opposite side of the open end of the blade holding portion 22, an attachment portion 22a having two engaging holes 22b is provided. As shown in FIG. 10, an upper end of the attachment portion 22a is tapered at the same angle as the inclined angle of the distal end portion of the coupler 3c (see FIG. 6). The aforementioned attachment/detachment mechanism portion 201 is made of the attachment portion 22a having the two engaging holes 22b. Thus, the head unit 200 is attached to the holding part 150 of the holder unit 100 as shown in FIG. 3, by the attachment portion 22a fitting into the holes 100c, the engaging holes 22b engaging the couplers 3c of the movable member 3, and the movable members 3 being biased toward the holes 100c by means of the compression spring 4. By moving the lever 3a (movable member 3) in the direction opposite to the holes 100c against the biasing force of the compression spring 4, the couplers 3c and the engaging holes 22b are disengaged, and thus the head unit 200 is removed from the holding part 150 of the holder unit 100.

Figure 9:
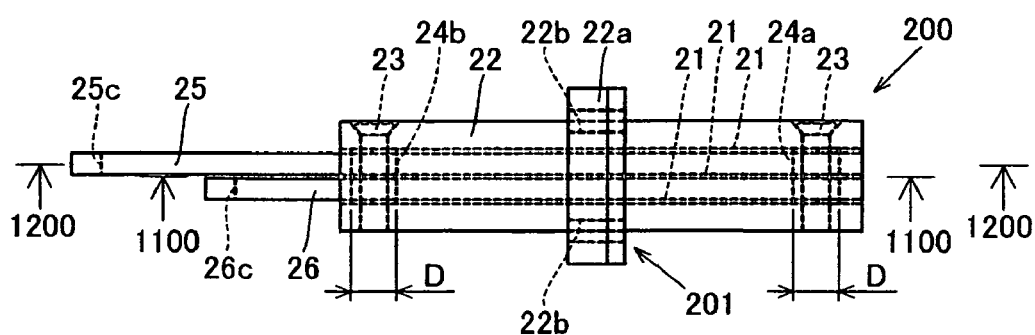
[FIG. 9] A plan view of a head of the tissue cutting device according to one embodiment shown in FIGS. 1 and 2.
Figure 10:
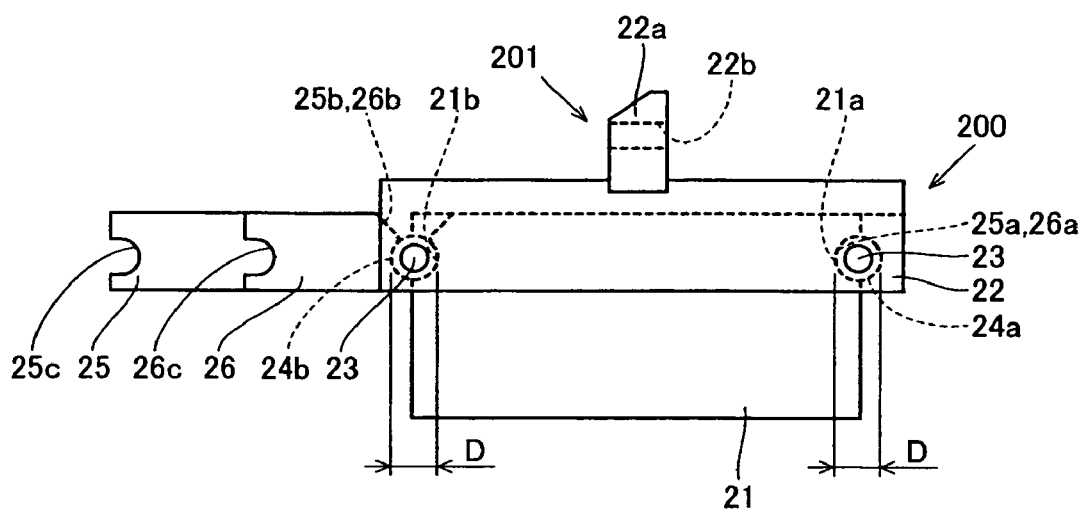
[FIG. 10] A side view of a head unit of the tissue cutting device according to one embodiment shown in FIGS. 1 and 2.
Figure 11:
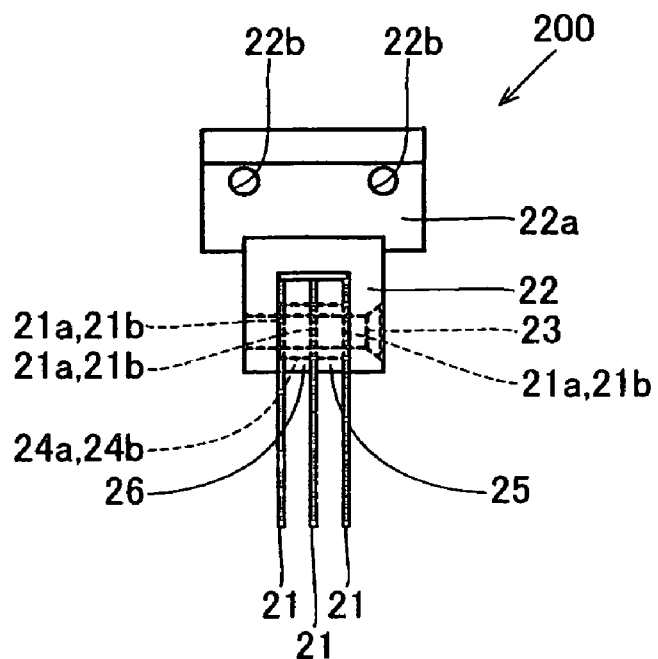
[FIG. 11] A front view of a head unit of the tissue cutting device according to one embodiment shown in FIGS. 1 and 2.

As shown in FIGS. 9 and 10, inside one and the other ends of the blade holding portion 22 formed into a square-U shape, cylindrical spacers 24a and 24b are respectively attached by a screw 32. These cylindrical spacers 24a and 24b have an outer diameter D of about 4 mm.

Figure 12:
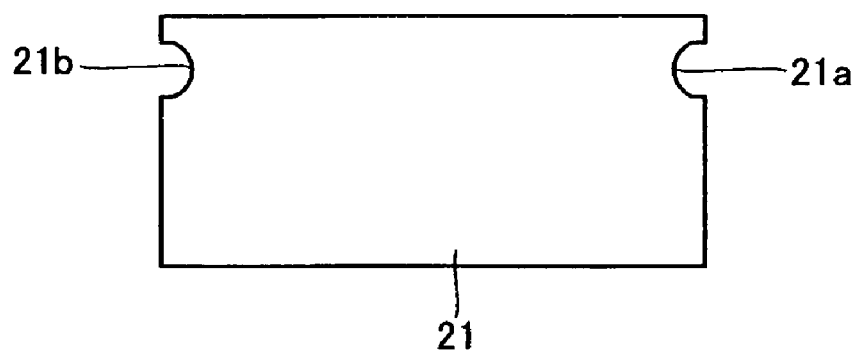
[FIG. 12] A side view of a blade of a head unit of the tissue cutting device according to one embodiment shown in FIGS. 1 and 2.
Figure 13:
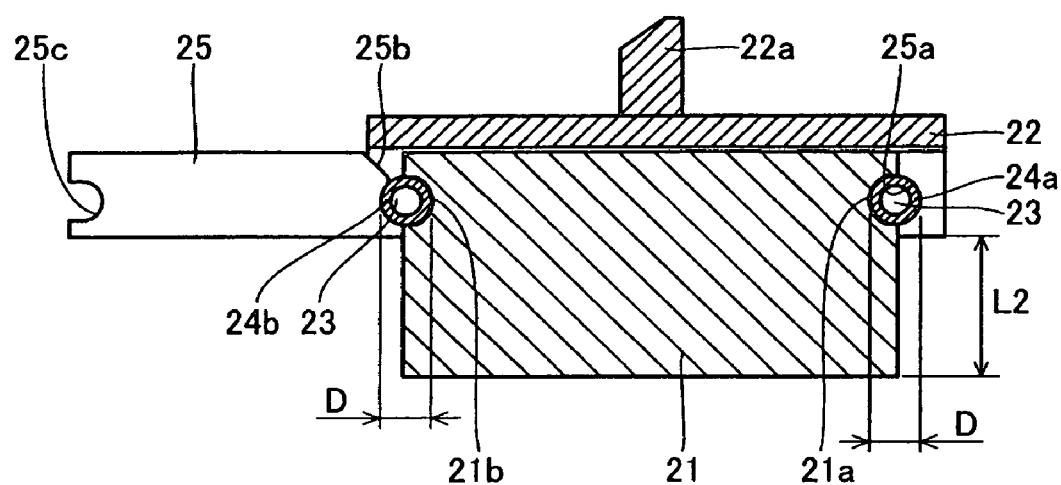
[FIG. 13] A sectional view seen along the line 1100-1100 in FIG. 9.

In the present embodiment, as shown in FIG. 12, fixing notches 21a and 21b are respectively formed on both ends along the longitudinal direction of the blade 21. As shown in FIG. 13, the blade 21 is fixed to the blade holding portion 22 by the notches 21a and 21b of the blade 21 respectively engaging the cylindrical spacers 24a and 24b. Since the blade 21 of the present embodiment is fixed to the blade holding portion 22 by means of the notches 21 and 21b, it is not necessary to provide the blade 21 of the present embodiment with a punch hole for fixation in the part where it contacts a biological tissue in cutting of the biological tissue. The three blades 21 each are about 0.1 mm thick. A distance L2 from a blade edge of each of the blades 21 to the bottom face of the blade holding portion 22 is about 11 mm.

Figure 14:
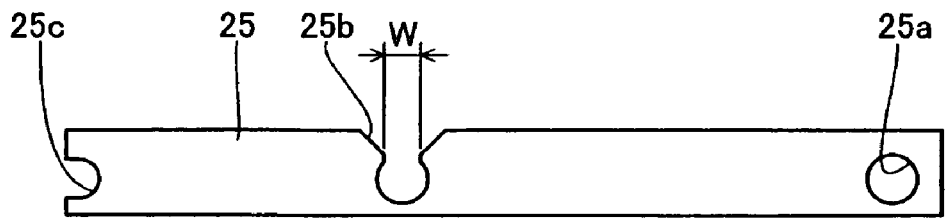
[FIG. 14] A side view of a spacer of a head unit of the tissue cutting device according to one embodiment shown in FIGS. 1 and 2.

In the present embodiment, as shown in FIGS. 9 to 11, the head unit 200 includes two spacers 25 and 26 for keeping an interval between adjacent blades 21 of the three blades. These two spacers 25 and 26 are longer in the longitudinal direction than the blade holding portion 22, and have different longitudinal lengths from each other. In the present embodiment, the longitudinal length of the spacer 25 is longer than the longitudinal length of the spacer 26. The spacers 25 and 26 have thicknesses of about 2 mm. As shown in FIG. 14, the spacer 25 has an attachment hole 25a, a notch 25b and a tab 25c. The attachment hole 25a is disposed on one end part in the longitudinal direction of the spacer 25, and has such an inner diameter that allows a cylindrical spacer 24a (see FIG. 15) to be fitted. The notch 25b is disposed between one end and the other end along the longitudinal direction of the spacer 25. The notch 25b is formed on the side of its open end with a tapered portion having an open width increasing as it goes closer to the open, and formed on the side opposite to its open end, with a circular portion. The circular portion of the notch 25b has such an inner diameter that allows the cylindrical spacer 24b (see FIG. 15) to be fitted therein. The portion where the taper forming portion and the circular portion connect with each other in the notch 25b has a width W of about 3.4 mm which is smaller than the outer diameter D (about 4 mm) of the cylindrical spacer 24b. The tab 25c is disposed on the other end part in the longitudinal direction of the spacer 25, and enables the spacer 25 to be gripped with tweezers or the like. As shown in FIG. 10, the spacer 26 has an attachment hole 26a, a notch 26b and a tab 26c which are similar to the attachment hole 25a, the notch 25b and the tab 25c of the spacer 25. As shown in FIGS. 9 and 11, the spacers 25 and 26 are respectively disposed between adjacent blades 21 of the three blades 21. Accordingly, intervals of the three blades 21 are about 2 mm.

Figure 15:
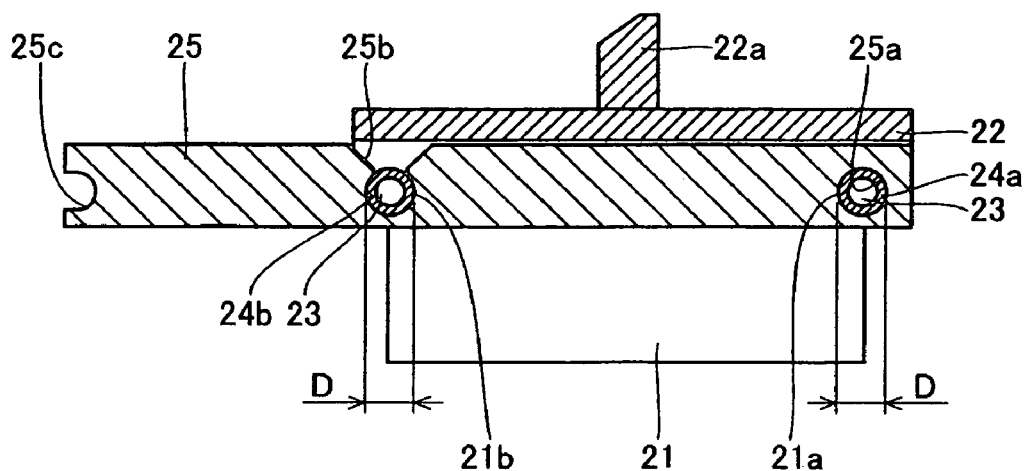
[FIG. 15] A sectional view seen along the line 1200-1200 in FIG. 9.
Figure 16:
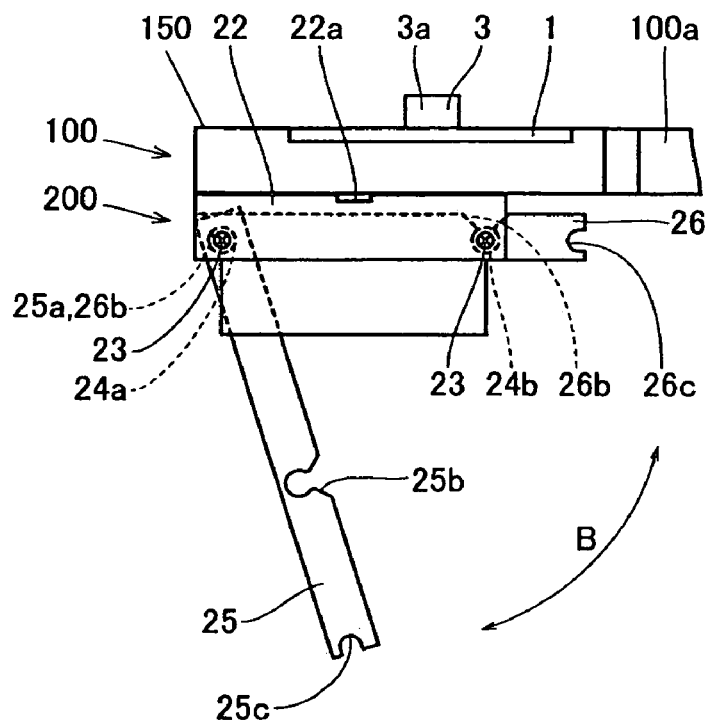
[FIG. 16] A side view of a spacer of a head unit in swiveled state of the tissue cutting device according to one embodiment shown in FIGS. 1 and 2.
Figure 17:
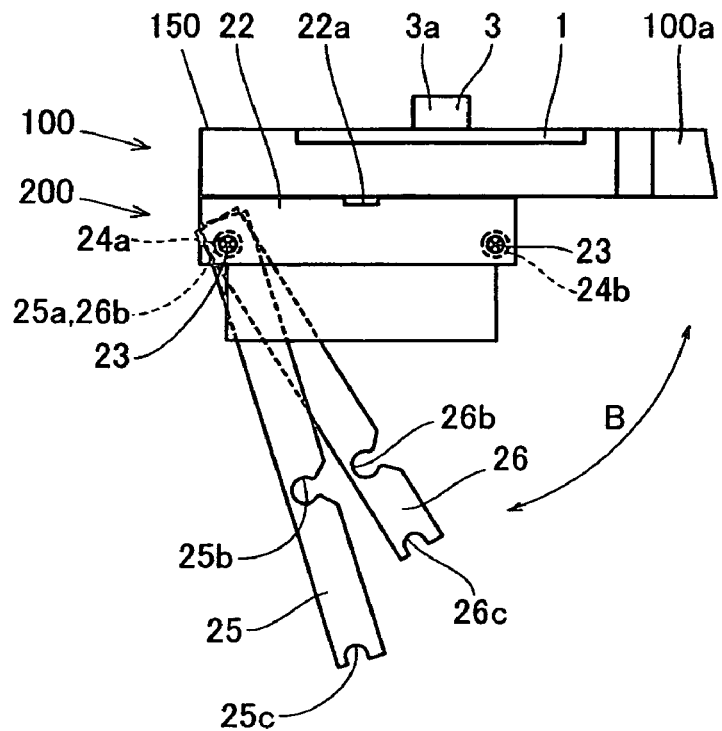
[FIG. 17] A side view of a spacer of a head unit in swiveled state of the tissue cutting device according to one embodiment shown in FIGS. 1 and 2.

Thus, as shown in FIG. 15, the spacer 25 is fixed to the blade holding portion 22 by the cylindrical spacer 24a fitted into the attachment holes 25a of the spacer 25, and by the cylindrical spacer 24b engaged with the notch 25b. As is the case with the spacer 25 and as shown in FIG. 10, the spacer 26 is fixed to the blade holding portion 22 by the cylindrical spacer 24a fitted into the attachment holes 26a of the spacer 26, and by the cylindrical spacer 24b engaged with the notch 26b. As shown in FIGS. 9 and 10, the end parts in which the tabs 25c and 26c of the spacers 25 and 26 are disposed so as to project from an end on the side of the cylindrical spacer 24b of the blade holding portion 22. And, as shown in FIG. 16, by applying downward force while gripping the tab 25c with tweezers (not shown) to disengage the notch 25b of the spacer 25 from the cylindrical spacer 24b, the spacer 25 is allowed to swivel in a B direction about the cylindrical spacer 24a. Further, as shown in FIG. 17, by applying downward force while gripping the tab 26c with tweezers (not shown) to disengage the notch 26b of the spacer 26 from the cylindrical spacer 24b, the spacer 26 is allowed to swivel in the B direction about the cylindrical spacer 24a.

In the tissue cutting device of the present embodiment, as described above, since the head unit 200 attached to the holding part 150 on the side of distal end of the holder unit 100 is configured to include three blades 21 arranged to extend parallel with the longitudinal direction (A direction) of the holder unit 100, and the blade holding portion 22 for holding the three blades 21, it is possible to split a biological tissue into four sections by one cutting operation, and hence to improve the efficiency of the cutting operation in splitting a biological tissue into four sections. Additionally, by arranging three blades at intervals of about 2 mm, it is possible to split a biological tissue into a section of the thickness as same as the interval of the blades 21 (about 2 mm), so that an equal thickness (about 2 mm) is realized for two sections in the four sections resulting from splitting of the biological tissue.

In the tissue cutting device of the present embodiment, by providing the holding part 150 of the holder unit 100 and the head unit 200 with the attachment/detachment mechanism portions 101 and 201 respectively so as to allow attachment/detachment of the head unit 200 to/from the holder unit 100, it is possible to readily replace a used head unit 200 (blade 21) attached to the holding part 150 of the holder unit 100 with a new head unit 200 (blade 21).

In the tissue cutting device of the present embodiment, by attaching the movable member 3 having the coupler 3c to the holding part 150 on the distal end side of the holder unit 100 so as to be movable along the longitudinal direction (A direction) of the holder unit 100, and by providing the attachment portion 22a having the engaging hole 22b configured to engage the coupler 3c on an upper part on the side opposite to the side where the blade 21 of the blade holding portion 22 constituting the head unit 200 is held, thereby bringing the coupler 3c of the holding part 150 of the holder unit 100 into engagement with the engaging hole 22b, it is possible to readily attach the head unit 200 to the holder unit 100. By disengaging the coupler 3c of the holding part 150 of the holder unit 100 from the engaging hole 22b of the head unit 200, it is possible to readily detach the head unit 200 from the holding part 150 of the holder unit 100.

In the tissue cutting device of the present embodiment, by configuring the blade holding portion 22 to include the spacers 25 and 26 for keeping intervals of three blades 21 at about 2 mm, it is possible to readily keep the interval between each set of adjacent blades 21 of the three blades 21 at about 2 mm by means of the spacers 25 and 26.

In the tissue cutting device of the present embodiment, the spacers 25 and 26 have a larger longitudinal length than the blade holding portion 22, the attachment holes 25a and 26a positioned in one end part along the longitudinal direction of the spacers 25 and 26 are attached to the cylindrical spacer 24a situated in one end of the blade holding portion 22 in a swivelable manner, and the tabs 25c and 26c situated in the other end part along the longitudinal direction of the spacers 25 and 26 are disposed so as to project from the other end part along the longitudinal direction of the blade holding portion 22. Accordingly, when a section of biological tissue is sandwiched between three blades 21 after cutting operation, by swiveling the spacers 25 and 26 about one end part along the longitudinal direction of the spacers 25 and 26 attached to the blade holding portion in a swivelable manner, it is possible to readily remove the section of biological tissue sandwiched between the blades 21 because the section of the biological tissue sandwiched between the blades 21 is pushed out by the spacers 25 and 26. Additionally, since the tabs 25c and 26c of the spacers 25 and 26 project from the other end part along the longitudinal direction of the blade holding portion 22, by applying force by gripping ends of the tabs 25c and 26c of the spacers 25 and 26 with tweezers, it is possible to make the spacers 25 and 26 swivel. Additionally, by making the longitudinal length of the spacer 25 larger than that of the spacer 26, it is possible to make the positions of the tab 25c of the spacer 25 and the tab 26c of the spacer 26 out of alignment before making the spacer 25 (26) swivel, and it is possible to make the tab 25c of the spacer 25 and the tab 26c of the spacer 26 to be difficult to be simultaneously gripped by tweezers. Consequently, the spacer 25 and the spacer 26 are difficult to pivot simultaneously, and hence it is possible to prevent split sections of biological tissue from contacting and combining with each other that would otherwise result from the sections of biological tissue sandwiched between the spacer 21 pushed out by the spacer 25 and the spacer 26 concurrently.

In the tissue cutting device of the present embodiment, by using the blade 21 having the notches 21a and 21b for fixation respectively on either end along the longitudinal direction, there is no need to provide a punch hole for fixation in the part where it contacts a biological tissue in cutting the biological tissue. As a result, occurrence of a trouble is prevented that structure of a biological tissue is broken in cutting the biological section due to contact between a punch hole of the blade 21 and the biological tissue. Additionally, by selecting the distance L2 from the blade edge of the blade 21 to the bottom face of the blade holding portion 22 at about 11 mm, occurrence of a trouble is prevented that a biological tissue is crushed by contact with the blade holding portion 22 in cutting the biological tissue, that would otherwise result from too small distance to the bottom face of the blade holding portion 22. Also, by selecting the thickness of the blade 21 at about 0.1 mm, occurrence of a trouble is prevented that structure of a biological tissue is broken in cutting the biological tissue, that would otherwise result from too large thickness of the blade 21.

In the tissue cutting device of the present embodiment, since the holding part 150 on the distal end side of the holder unit 100 is provided with the two water-discharge holes 100e connecting to the recess 10b, it is possible to prevent washing water from pooling in the recess 100b during washing of the holder unit 100 with the washing water after cutting of the biological tissue, and hence it is possible to readily dry the holder unit 100 after washing.

Figure 18:
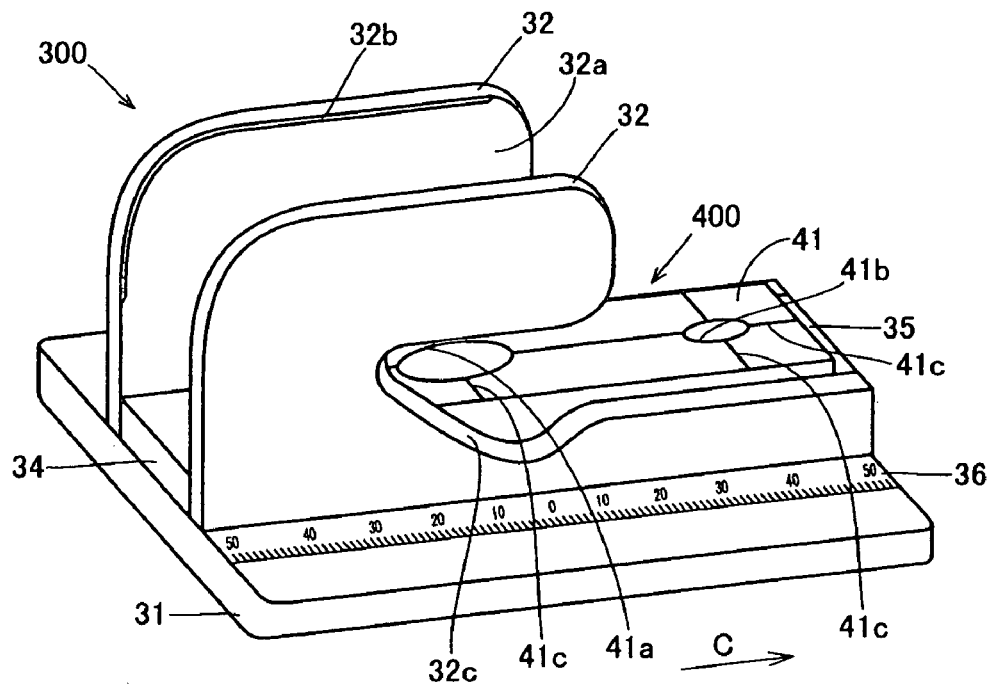
[FIG. 18] A perspective view of a tissue cut assisting device according to one embodiment of the present invention.
Figure 19:
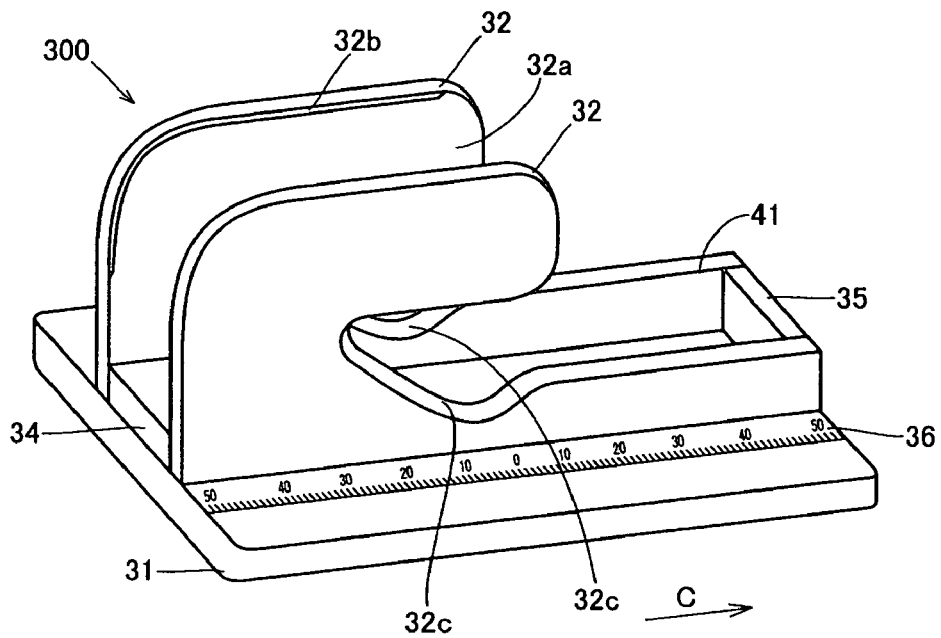
[FIG. 19] A perspective view of a base of the tissue cut assisting device according to one embodiment shown in FIG. 18.
Figure 20:
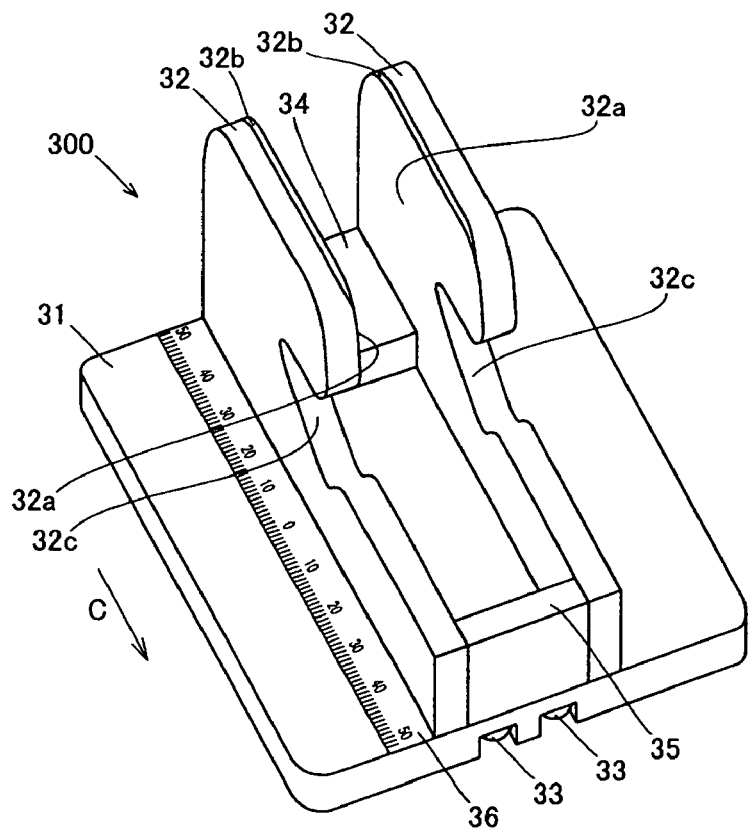
[FIG. 20] A perspective view of a base of the tissue cut assisting device according to one embodiment shown in FIG. 18.
Figure 21:
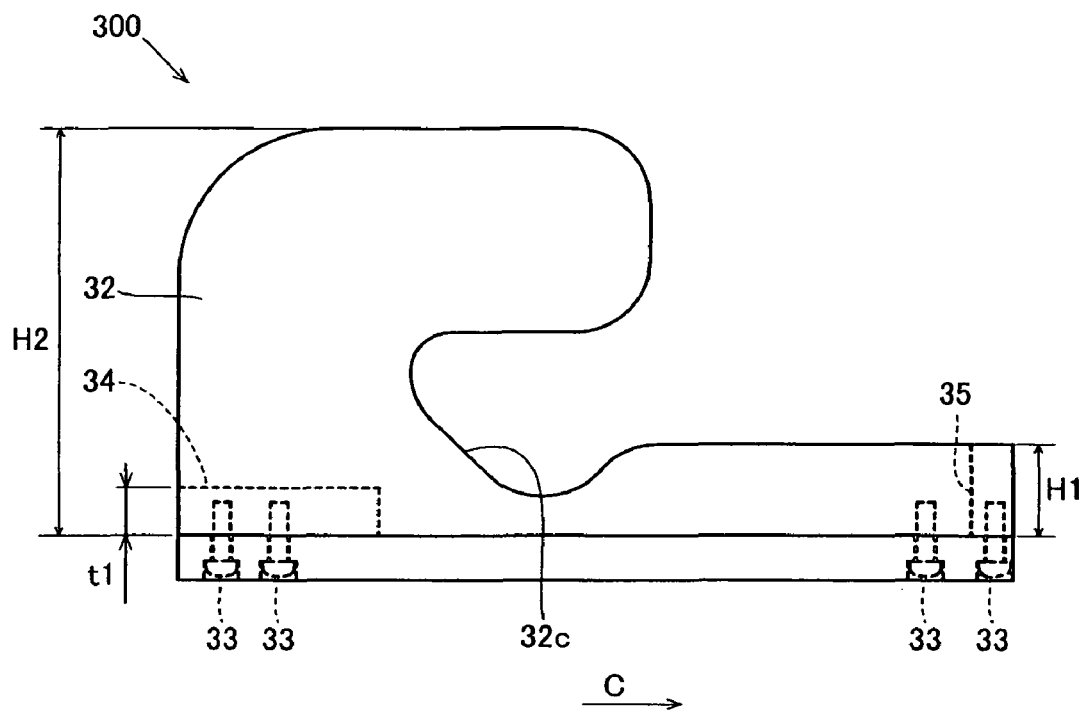
[FIG. 21] A side view of a base of the tissue cut assisting device according to one embodiment shown in FIGS. 19 and 20.
Figure 22:
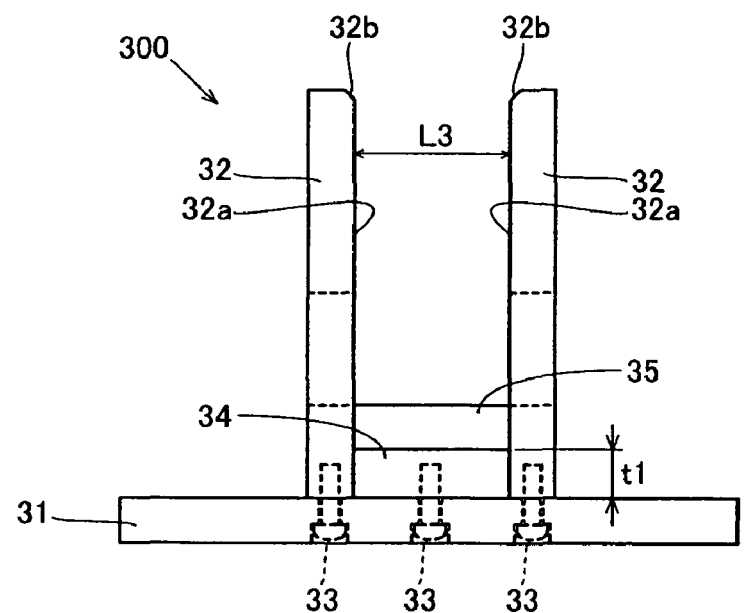
[FIG. 22] A front view of a base of the tissue cut assisting device according to one embodiment shown in FIGS. 19 and 20.
Figure 23:
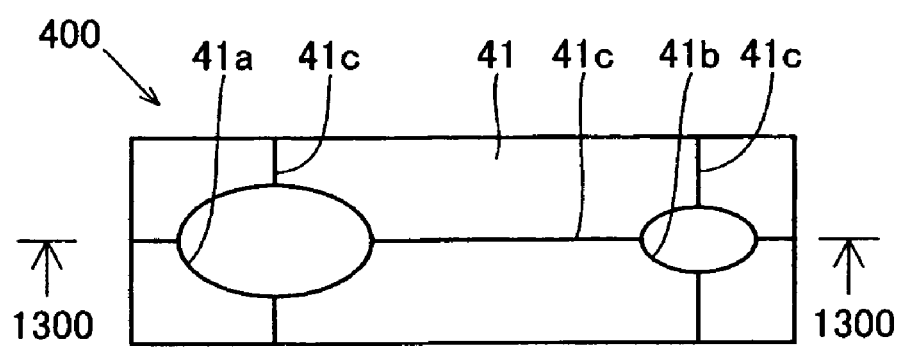
[FIG. 23] A plan view of a mounting member of the tissue cut assisting device according to one embodiment shown in FIG. 18.
Figure 24:
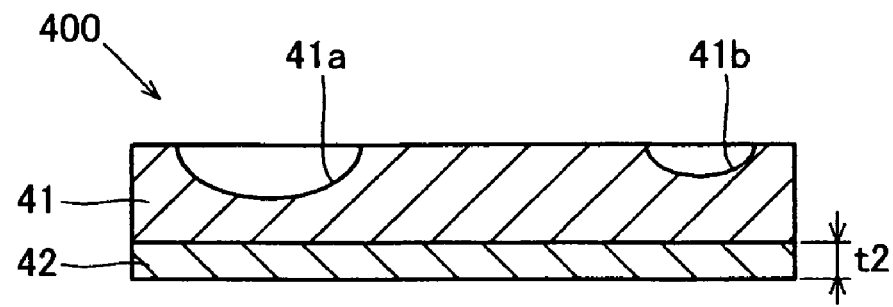
[FIG. 24] A sectional view seen along the line 1300-1300 in FIG. 23.

FIG. 18 is a perspective view showing a tissue cut assisting device according to one embodiment of the present invention, FIGS. 19 and 20 are perspective views showing a pedestal of the tissue cut assisting device according to one embodiment shown in FIG. 18. FIG. 21 and FIG. 22 are respectively a side view and a front view of the pedestal of the tissue cut assisting device according to one embodiment shown in FIGS. 19 and 20. FIG. 23 is a front view of a mounting member of the tissue cut assisting device according to one embodiment shown in FIG. 18, FIG. 24 is a sectional view along the line 1300-1300 in FIG. 23. Now referring to FIGS. 18 to 24, explanation will be made on a tissue cut assisting device for assisting a cutting operation of a biological tissue using the tissue cutting device for cutting a biological tissue according to the present embodiment. The direction of the arrow C) in FIGS. 18 to 21 indicates the cutting direction in which a biological tissue is cut by the use of a tissue cutting device.

As shown in FIG. 18, the tissue cut assisting device of the present embodiment has a pedestal 300 and a mounting member 400. As shown in FIGS. 18 to 20, in a concrete structure of the pedestal 300, a pair of guiding members 32 are attached on the base 31 at a predetermined interval. The pair of guiding members 32 guide a tissue cutting device during a cutting operation of a biological tissue by the aforementioned tissue cutting device. Further, an interval L3 (see FIG. 22) between guiding surfaces 32a of the pair of guiding members 32 is configured to have a length larger by about 0.1 mm to about 0.3 mm than a width length L1 (see FIG. 7) of the holding part 150 in the distal end part of the holder unit 100 of the tissue cutting device. In the present embodiment, the interval L3 between the guiding surfaces 32a of the pair of guiding members 32 is set at about 20 mm. At a predetermined position between the pair of guiding members 32 on the base 31, the aforementioned mounting member 400 is replaceably mounted.

In the present embodiment, as shown in FIG. 21, a part on upstream side in the cutting direction (direction indicated by the arrow C) of the guiding member 32 has a height H2 which is larger than a height H1 of a part on downstream side in the cutting direction (direction indicated by the arrow C) of the guiding member 32. As shown in FIGS. 18 and 22, the guiding surface 32a of the guiding member 32 is partly formed in its upper part and rear part of its upstream part with a taper-shaped portion 32b of the guiding member 32. The guiding members 32 are formed of transparent vinyl chloride resin so that the mounting member 400 placed at a predetermined position between the pair of guiding members 32 can be visually observed through the guiding members 32. As shown in FIG. 21, in an upstream part of the guiding member 32 along the cutting direction (direction indicated by the arrow C), a notch 32c, which extends from downstream side to upstream side in the cutting direction (direction indicated by the arrow C) is formed. The guiding members 32 are attached to the base 31 from backside of the base 31 with screws 33.

In the present embodiment, as shown in FIG. 18 to FIG. 20, between the pair of guiding members 32 on the base 31, two positioning members 34 and 35 are attached. The positioning member 34 is disposed on upstream side in the cutting direction (direction indicated by the arrow C), while the positioning member 35 is disposed on downstream side in the cutting direction (direction indicated by the arrow C). These positioning members 34 and 35 position the mounting member 400 with respect to the base 31 and regulate movement of the mounting member 400 in the cutting direction (direction indicated by the arrow C). In the present embodiment, an interval between the positioning member 34 and the positioning member 35 is set at about 70 mm. The positioning member 34 disposed on upstream side of the cutting direction (direction indicated by the arrow C) has a sheet form and has a thickness t1 (see FIGS. 21 and 22) of about 6 mm. As shown in FIGS. 21 and 22, the positioning members 34 and 35 are attached to the base 31 from backside of the base 31 with screws 33. As shown in FIGS. 18 to 20, in a predetermined region on the top face of the base 31, a scale 36 is attached for measuring the size of a biological tissue to be cut.

In the present embodiment, as shown in FIG. 24, the mounting member 400 includes an urethane sponge member 41 that can be cut together with a biological tissue by the aforementioned tissue cutting device, and a supporting member 42 made of rigid urethane resin for supporting the urethane sponge member 41. As shown in FIG. 23, the urethane sponge member 41 is formed with two ellipsoidal recesses 41a and 41b having different two-dimensional sizes. In either one of the recesses 41a and 41b, a biological tissue to be cut is placed. The larger recess 41a has a long axial diameter of about 20 mm and a short axial diameter of about 12 mm, while the smaller recess 41b has a long axial diameter of about 12 mm and a short axial diameter of about 7 mm. On a top surface of the urethane sponge member 41, a center axial line 41c is printed so that respective centers of long axes and short axes of the recesses 41a and 41b can be visually checked. As shown in FIG. 24, the urethane sponge member 41 and the supporting member 42 are bonded together with a two-sided tape.

In the present embodiment, as shown in FIG. 21 and FIG. 24, the supporting member 42 constituting the mounting member 400 has a thickness t2 (about 5 mm) which is smaller the thickness t1 (about 6 mm) of the positioning member 34 (see FIG. 21) disposed on upstream side of the cutting direction (direction indicated by the arrow C). Accordingly, when the mounting member 400 is placed on the base 31, the top face of the positioning member 34 is at higher level than the top face of the supporting member 42.

In the tissue cut assisting device of the present embodiment, by disposing on the base 31 the pair of guiding members 32 for guiding a cutting operation of biological tissue by a tissue cutting device, and mounting the mounting member 400 for placement of a biological tissue in a predetermined position between the pair of guiding members 32 on the base 31 as described above, it is possible to regulate movement of the tissue cutting device along the direction perpendicular to the cutting direction (direction indicated by the arrow C) by means of the pair of guiding members 32 during cutting of a biological tissue mounted on the mounting member 400, so that it is possible to prevent the cutting direction from deviating. As a result, it is possible to readily cut a biological tissue by means of the tissue cutting device, and hence it is possible to improve the efficiency of cutting operation in splitting a biological tissue into a plurality of sections.

In the tissue cut assisting device of the present embodiment, as described above, by enabling the mounting member 400 to be mounted replaceably in a predetermined position between the pair of guiding members 32 on the base 31, it is possible to readily replace a used mounting member 400 placed in a predetermined position between the pair of guiding members 32 on the base 31 with a new mounting member 400, so that continuous use is possible only by replacement of the mounting member 400.

In the tissue cut assisting device of the present embodiment, by positioning the mounting member 400 with respect to the base 31, and by disposing the positioning members 34 and 35 for regulating movement of the mounting member 400 in the cutting direction (direction indicated by the arrow C) respectively on upstream and downstream sides of the cutting direction (direction indicated by the arrow C), it is possible to prevent the mounting member 400 from moving upstream along the cutting direction (direction indicated by the arrow C) by to the positioning member 34, and it is possible to prevent the mounting member 400 from moving downstream along the cutting direction (direction indicated by the arrow C) by the positioning member 35 when a biological tissue placed on the mounting member 400 is cut. As a result, it is possible to cut a biological tissue more readily by the tissue cutting device, and hence it is possible to improve the efficiency of cutting operation in splitting a biological tissue into a plurality of sections.

In the tissue cut assisting device of the present embodiment, by making the positioning member 34 disposed on upstream side of the cutting direction (direction indicated by the arrow C) into a sheet form, and making thickness t1 (about 6 mm) of the positioning member 34 larger than thickness t2 (about 5 mm) of the supporting member 42 constituting the mounting member 400, thereby making the top face of the positioning member 34 at higher level than the top face of the supporting member 42, it is possible to prevent occurrence of a trouble that the blade 21 of the tissue cutting device is difficult to move in the cutting direction (direction indicated by the arrow C) due to the fact that the blade 21 of the tissue cutting device cuts into a corner part of the supporting member in the boundary between the positioning member 34 and the supporting member 42 when the blade 21 of the tissue cutting device is moved along the top face of the supporting member 42 following the top face of the positioning member 34 in the cutting direction (direction indicated by the arrow C) in cutting a biological tissue placed on the mounting member 400.

In the tissue cut assisting device of the present embodiment, by forming the taper-shaped portion 32b in a part of upper part and rear part on upstream side of the guiding surface 32a of the guiding member 32, occurrence of a trouble can be avoided that the tissue cutting device is difficult to be inserted between the pair of guiding members 32 resulting from the fact that the tissue cutting device is caught by a corner of an upper part of the guiding surface 32a of the guiding member 32 in inserting the tissue cutting device into the pair of guiding members 32.

In the tissue cut assisting device of the present embodiment, by forming the pair of guiding members 32 of a material that allows mounting member 400 to be visually checked through the guiding members 32 (transparent vinyl chloride resin), it is possible to place a biological tissue on the mounting member 400 while visually checking the mounting member 400 through the guiding members 32 and hence a biological tissue can be reliably placed on the mounting member 400. Further, by forming the notch 32c which extends from downstream side to upstream side in the cutting direction (direction indicated by the arrow C) in upstream part in the cutting direction (direction indicated by the arrow C) of the guiding member 32, it is possible to readily adjust the position of a biological tissue placed on the mounting member 400 mounted between the pair of guiding members 32 with tweezers.

In the present embodiment, by attaching the pair of guiding members 32, the positioning members 34 and 35 to the base 31 from backside with screws 33, it is possible to prevent blood or the like from flowing into screw holes during cutting operation in contrast to the case where screw cramp is achieved from superficial side of the base 31, and the pedestal 300 can be readily washed with washing water.

In the tissue cut assisting device of the present embodiment, by configuring the mounting member 400 to include the urethane sponge member 41 having the recesses 41a and 41b for mounting a biological tissue thereon, and the supporting member 42 made of rigid urethane resin for supporting the urethane sponge member 41, in placing a biological tissue on the mounting member 400, it is possible to readily fix the biological tissue on the mounting member 400 via the recess 41a (41b) of the urethane sponge member 41 constituting the mounting member 400. When a biological tissue placed on the recess 41a (41b) of the urethane sponge member 41 is cut together with the urethane sponge member 41, since the urethane sponge member 41 is supported by the supporting member 42, it is possible to prevent deformation of the urethane sponge member 41. By providing the urethane sponge member 41 with the recesses 41a and 41b having different sizes, it is possible to select and use either the recess 41a or the recess 41b depending the size of the biological tissue, and hence the biological tissue can be fixed to the mounting member 400 more securely. Additionally, by providing the urethane sponge member 41 that can be cut by the tissue cutting device with the recesses 41a and 41b for placing a biological tissue thereon, it is possible to cut the biological tissue placed in the recess 41a (41b) of the urethane sponge member 41 together with the urethane sponge member 41, and hence the biological tissue placed on the mounting member 400 can be cut more easily. Since the urethane sponge member 41 generates much less cutting chips, it is possible to prevent adhesion of cutting chips to split sections of the biological tissue.

Figure 25:
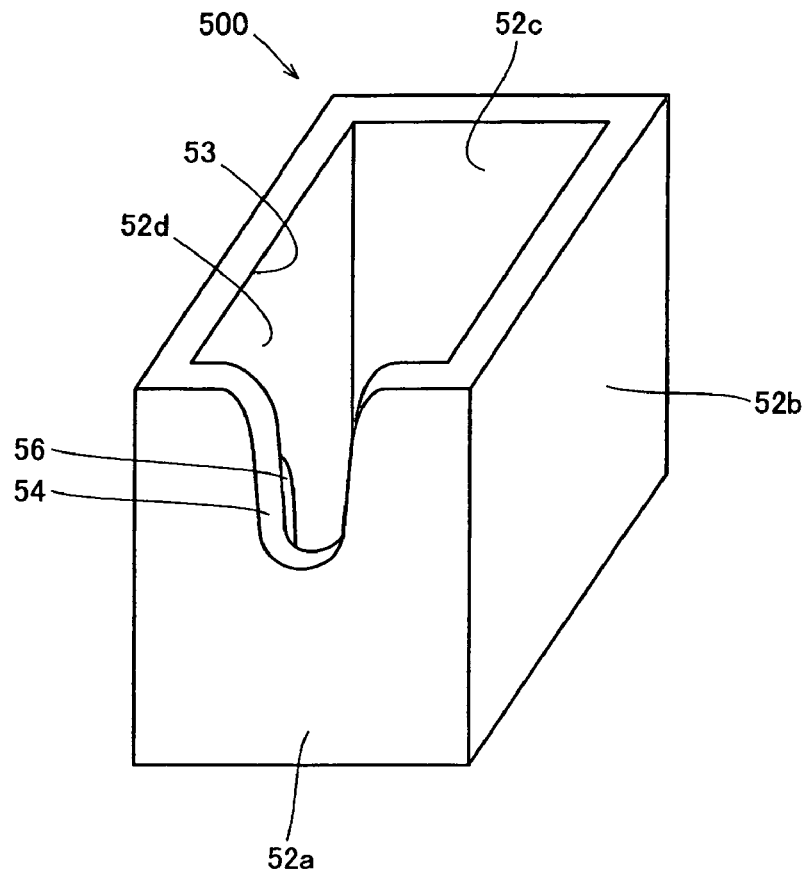
[FIG. 25] A perspective view of an accommodation housing according to one embodiment of the present invention.
Figure 26:
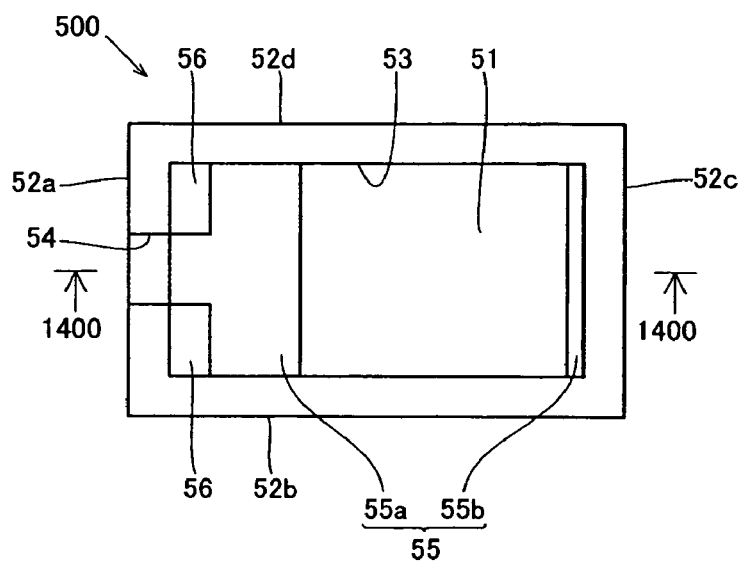
[FIG. 26] A plan view of the accommodation housing shown in FIG. 25.
Figure 27:
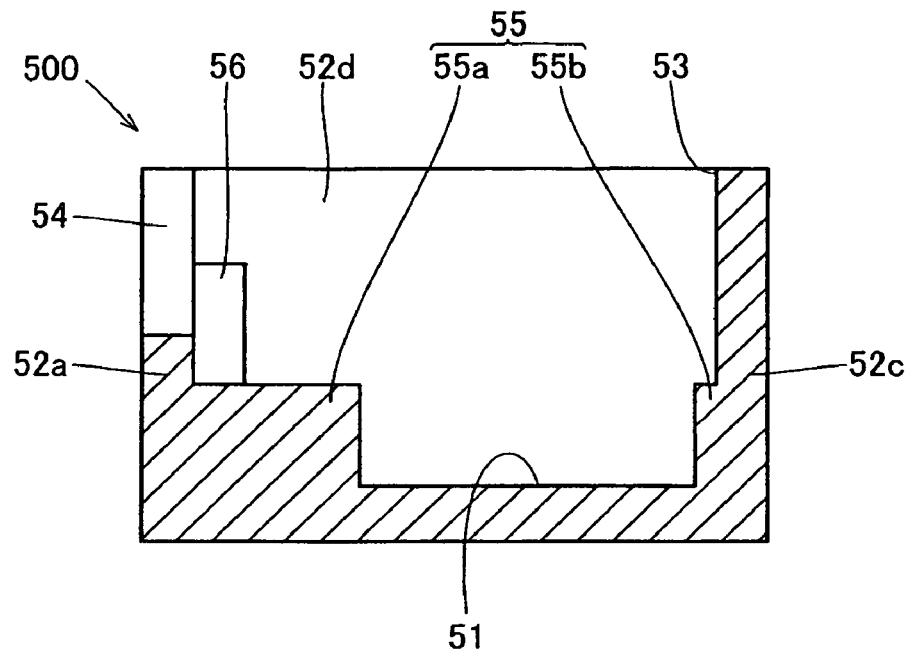
[FIG. 27] A sectional view seen along the line 1400-1400 in FIG. 26.
Figure 28:
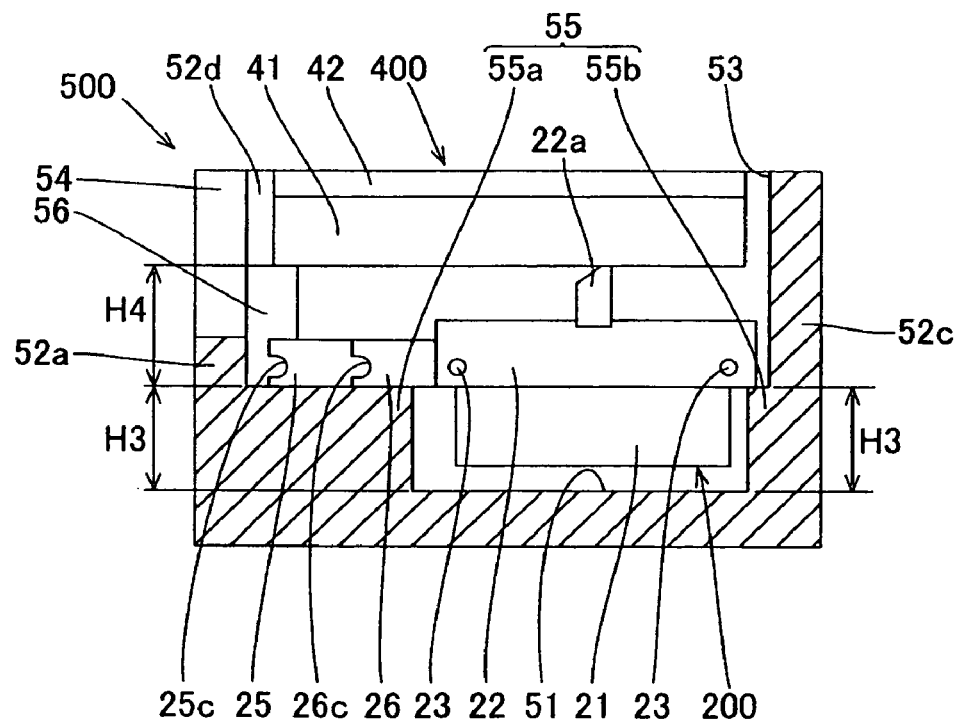
[FIG. 28] A sectional view showing the state that a head unit and a mounting member are accommodated in the accommodation housing shown in FIG. 25.

FIG. 25 is a perspective view showing an accommodation housing according to one embodiment of the present invention. FIG. 26 is a plan view of the accommodation housing according to one embodiment shown in FIG. 25, and FIG. 27 is a sectional view along the line 1400-1400 in FIG. 27. FIG. 28 is a sectional view showing the state in which a head unit and a mounting member are accommodated in the accommodation housing according to one embodiment shown in FIG. 25. Next, referring to FIGS. 25 to 28, explanation will be made on an accommodation housing for accommodating a head unit of the tissue cutting device for cutting a biological tissue according to the present embodiment.

As shown in FIGS. 25 to 27, an accommodation housing 500 of the present embodiment includes a bottom part 51, four lateral faces 52a to 52d extending upward from the bottom part 51, and an opening 53 formed at the upper part facing the bottom part 51 and facing the bottom part 51. One lateral face 52a of the accommodation housing 500 is formed with a U-shaped slit portion 54 in continuation with the opening 53 through which the holder unit 100 (see FIG. 33) of the tissue cutting device can be inserted from above. As shown in FIGS. 26 to 28, inside the accommodation housing 500, there is provided a head unit accommodating portion 55 for accommodating the blade 21 of the head unit 200 so as to face the bottom part 51. The head unit accommodating portion 55 includes a portion 55a disposed on the side of the lateral face 52a in which the slit portion 54 is formed, and a portion 55b disposed on the side of the lateral face 52c opposing to the lateral face 52a in which the slit portion 54 is formed. As shown in FIG. 28, when the head unit 200 is accommodated, the spacers 25 and 26 are placed on the portion 55a of the head unit accommodating portion 55, and the distal end of the blade holding portion 22 is placed on the top face of the portion 55b of the head unit accommodating portion 55. Height H3 of the portions 55a and 55b of the head unit accommodating portion 55 from the inner face of the bottom part 51 is set so that the blade 21 will not come into contact with the inner face of the bottom part 51 when the head unit 200 is accommodated.

In the present embodiment, as shown in FIGS. 26 to 28, in an upper region from the head unit accommodating portion 55 inside the accommodation housing 500, there is provided a mounting member accommodating portion 56 for accommodating the urethane sponge member 41 of the mounting member 400 so as to face the bottom part 51. The mounting member accommodating portion 56 is disposed only on the side of the lateral face 52a in which the slit portion 54 is formed. As shown in FIG. 28, height H4 of the mounting member accommodating portion 56 from the top face of the head unit accommodating portion 55 is set to be as same as the top face of the attachment portion 22a of the head unit 200 accommodated in the head unit accommodating portion 55. Consequently, when the mounting member 400 is accommodated, the mounting member 400 is supported by the mounting member accommodating portion 56 and the attachment portion 22a.

In the accommodation housing of the present embodiment, as described above, by providing the head unit accommodating portion 55 for accommodating the blade 51 of the head unit 200 so as to face the bottom part 51 while preventing the blade 21 of the head unit 200 from contacting the inner face of the bottom part 51, it is possible to accommodate the head unit 200 while preventing dusts or the like from adhering to the blade 21.

In the accommodation housing of the present embodiment, by forming the opening 53 above the bottom part 51 so as to face with the bottom part 51, and forming the U-shaped slit portion 54 in continuation with the opening 53 through which the holder unit 100 of the tissue cutting device can be inserted from above in the lateral face 52a extending upward from the bottom part 51, it is possible to insert the holder unit 100 into the accommodation housing 500 from above through the opening 53 and the slit portion 54, and hence it is possible to attach the head unit 200 accommodated in the accommodation housing 500 to the holder unit 100 without a touch to the head unit by operator's hands.

In the accommodation housing of the present embodiment, by providing the mounting member accommodating portion 56 for accommodating the mounting member 400 in a region above the head unit accommodating portion 55 inside the accommodation housing 500, it is possible to accommodate the mounting member 400 in the accommodation housing 500 more readily by the mounting member accommodating portion 56. By configuring the mounting member accommodating portion 56 so that the urethane sponge member 41 of the mounting member 400 can be accommodated to face the bottom part 51, it is possible to prevent dusts or the like from adhering to the recesses 41a and 41b formed in the urethane sponge member 41 for placement of a biological tissue.

Figure 29:
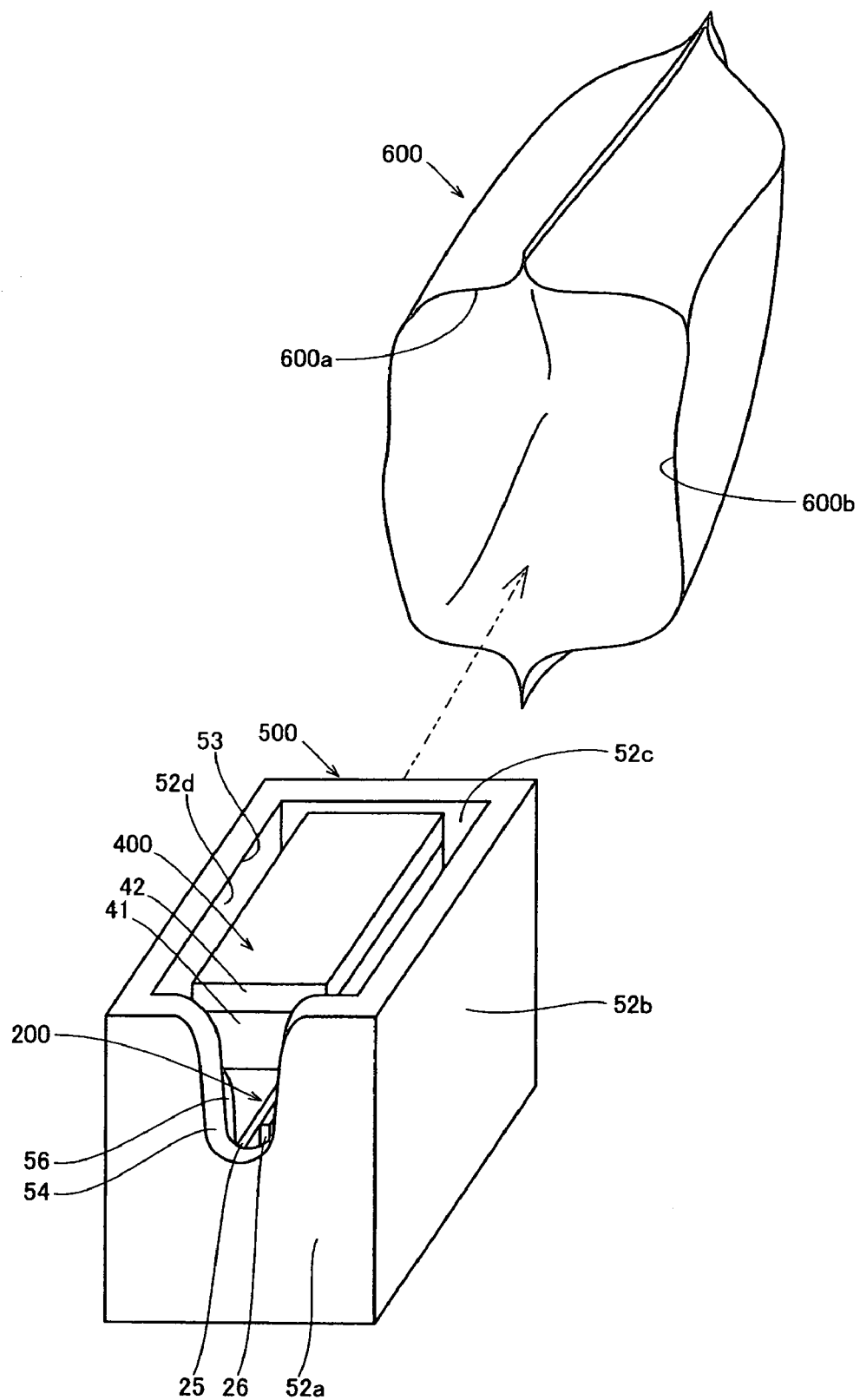
[FIG. 29] A perspective view of a storage bag according to one embodiment of the present invention.
Figure 30:
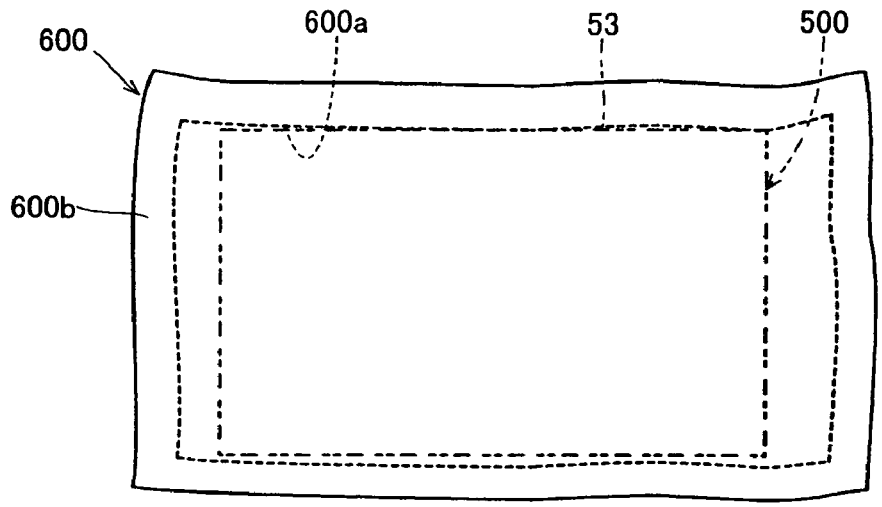
[FIG. 30] A side view showing the state that an accommodation housing is stored in the storage bag according to one embodiment shown in FIG. 29.

FIG. 29 is a perspective view of a storage bag according to one embodiment of the present invention, FIG. 30 is a side view showing the state in which the accommodation housing is stored in the storage bag according to one embodiment shown in FIG. 29. Next, referring to FIGS. 29 and 30, explanation will be made on a storage bag 600 for storing an accommodation housing according to the present embodiment.

As shown in FIG. 29, the storage bag 600 of the present embodiment is capable of store the accommodation housing 500 accommodating the head unit 200 and the mounting member 400. To be more specific, the storage bag 600 is formed from a polyethylene bag processed to be openable at an arbitrary position. As shown in FIG. 30, when the accommodation housing 500 is stored, an inner face 600a of the storage bag 600 functions as a lid for closing the opening 53 of the accommodation housing 500. When the accommodation housing 500 is stored, the storage bag 600 is heat sealed at an opening 600b with the internal air of the storage bag 600 evacuated.

In the present embodiment, as described above, by storing the accommodation housing 500 in the storage bag 600 in which the inner face 600a functions as a lid closing the opening 53 of the accommodation housing 500, it is possible to prevent the head unit 200 and the mounting member 400 from leaving outside the accommodation housing 500. Further, by forming the storage bag 600 from a polyethylene bag that is processed so as to be openable at an arbitrary position, the storage bag 600 may be opened at an arbitrary position, resulting that it is possible to reduce the operator's labor for opening the bag.

Figure 35:
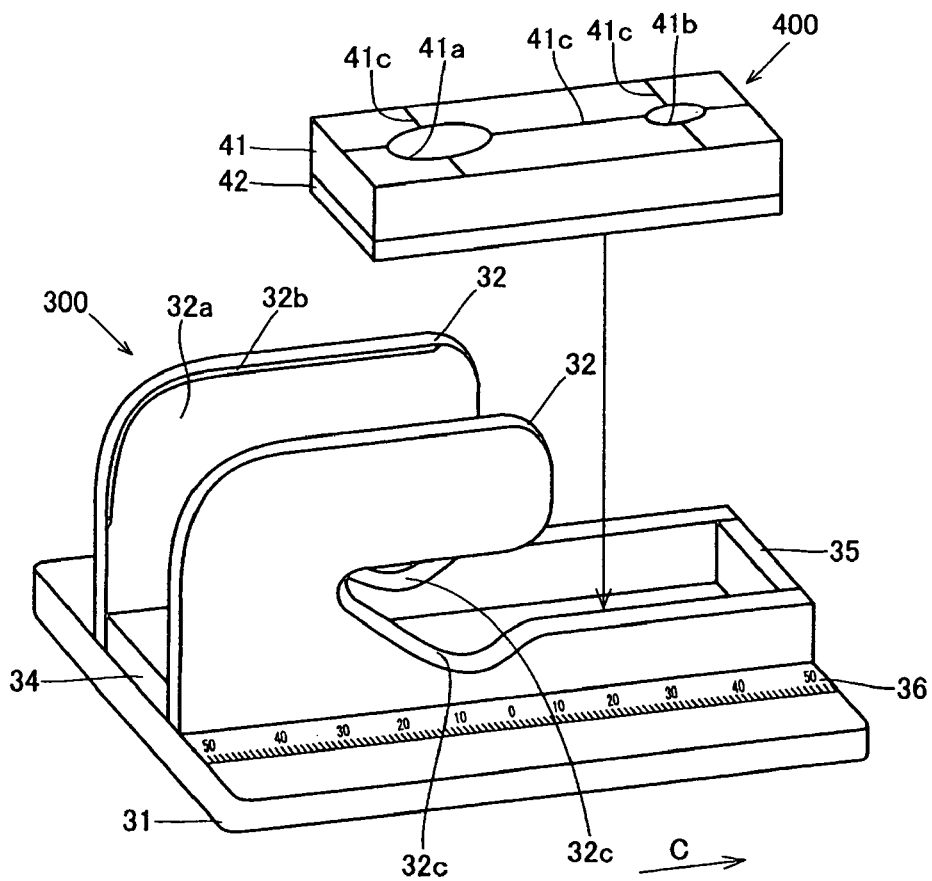
[FIG. 35] A perspective view for illustrating an operation of mounting a biological tissue on a mounting member of a tissue cut assisting device according to one embodiment of the present invention.
Figure 36:
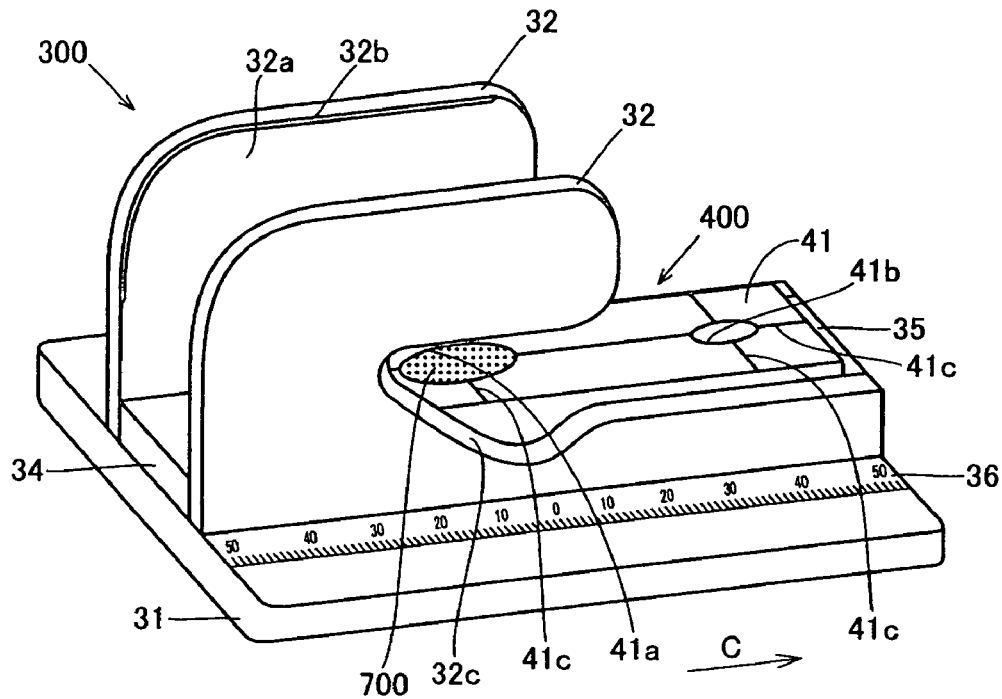
[FIG. 36] A perspective view for illustrating an operation of mounting a biological tissue on a mounting member of a tissue cut assisting device according to one embodiment of the present invention.
Figure 37:
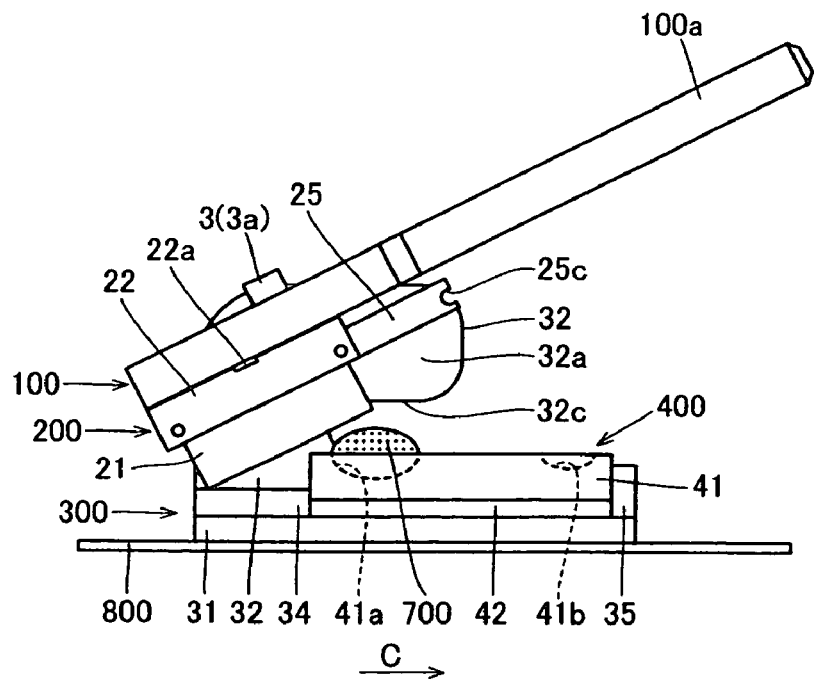
[FIG. 37] A schematic view for illustrating an operation of cutting a biological tissue using a tissue cutting device according to one embodiment of the present invention.
Figure 38:
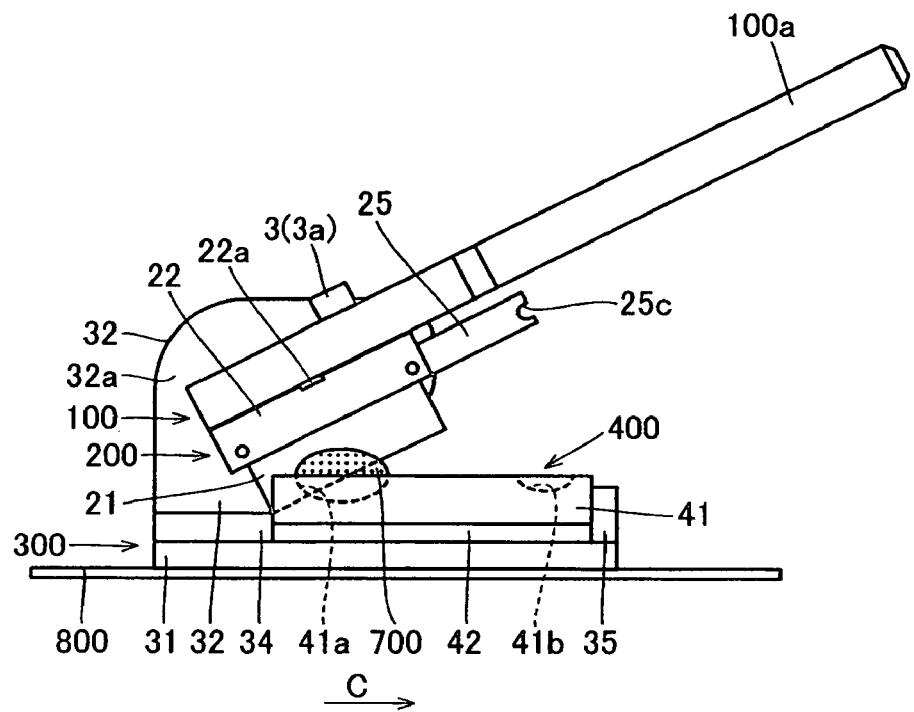
[FIG. 38] A schematic view for illustrating an operation of cutting a biological tissue using a tissue cutting device according to one embodiment of the present invention.
Figure 39:
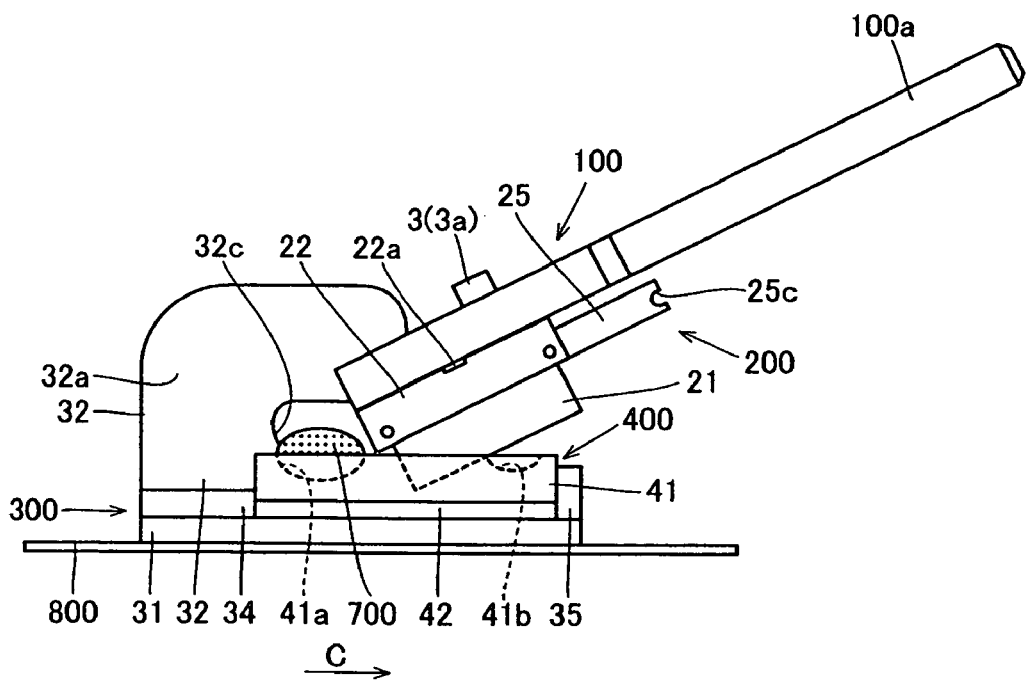
[FIG. 39] A schematic view for illustrating an operation of cutting a biological tissue using a tissue cutting device according to one embodiment of the present invention.
Figure 40:
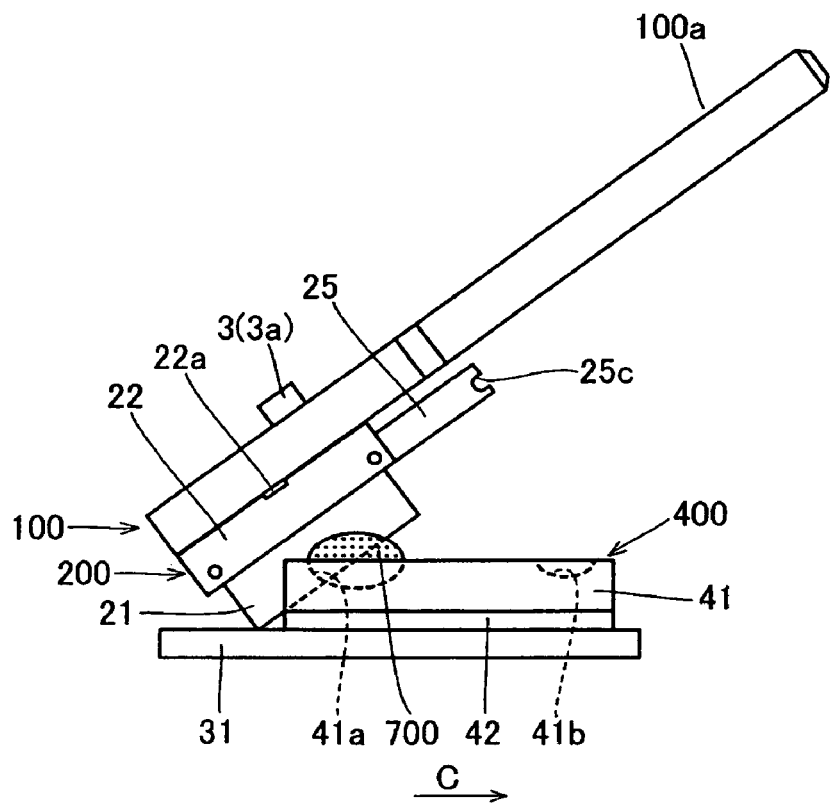
[FIG. 40] A schematic view showing a state in which a blade of a tissue cutting device bites into a mounting member.
Figure 41:
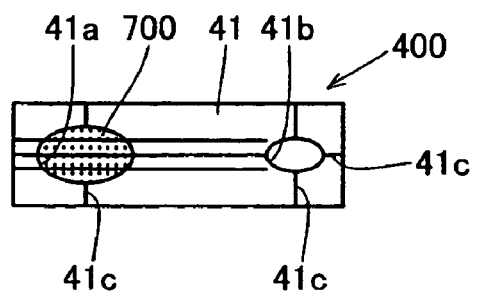
[FIG. 41] A plan view showing a biological tissue cut with a tissue cutting device according to one embodiment of the present invention.

FIGS. 31 to 34 are perspective views and schematic views for explaining an attaching operation of a head unit to a holder unit of a tissue cutting device according to one embodiment of the present invention. FIGS. 35 and 36 are perspective views for explaining an operation of placing a biological tissue on a mounting member of a tissue cut assisting device according to one embodiment of the present invention. FIGS. 37 to 39 are schematic views for explaining an operation of cutting a biological tissue using a tissue cutting device of the present embodiment. FIG. 40 is a schematic view showing the state in which a blade of a tissue cutting device is cut into a mounting member. FIG. 41 is a plan view of a biological tissue cut by a tissue cutting device according to one embodiment of the present invention. Next, referring to FIG. 28 and FIGS. 30 to 41, explanation will be made on an attaching operation of a head unit to a holder unit, a placing operation of a biological tissue on to a mounting member, and a cutting operation of a biological tissue. In the present embodiment, explanation is made while taking a case of cutting a lymph node as an example.

First, the storage bag 600 storing the accommodation housing 500 shown in FIG. 30 is opened. After removing the accommodation housing 500 from the storage bag 600, the mounting member 400 (see FIG. 28) is removed from the accommodation housing 500.

Figure 31:
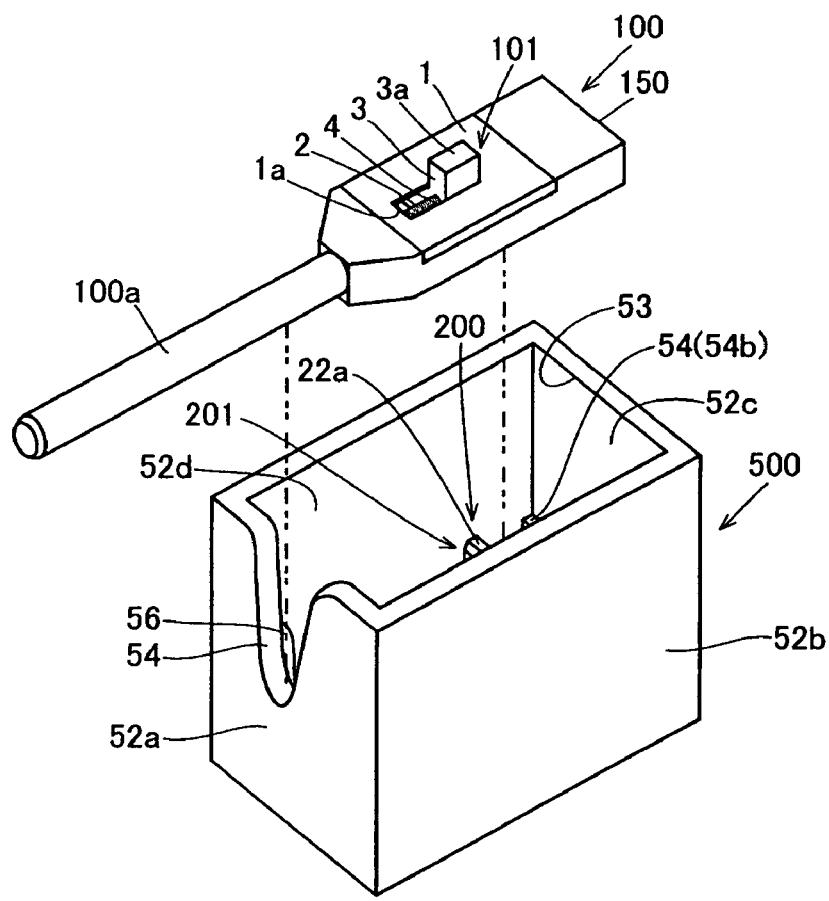
[FIG. 31] A perspective view for illustrating an attaching operation of a head unit to a holder unit of a tissue cutting device according to one embodiment of the present invention.
Figure 32:
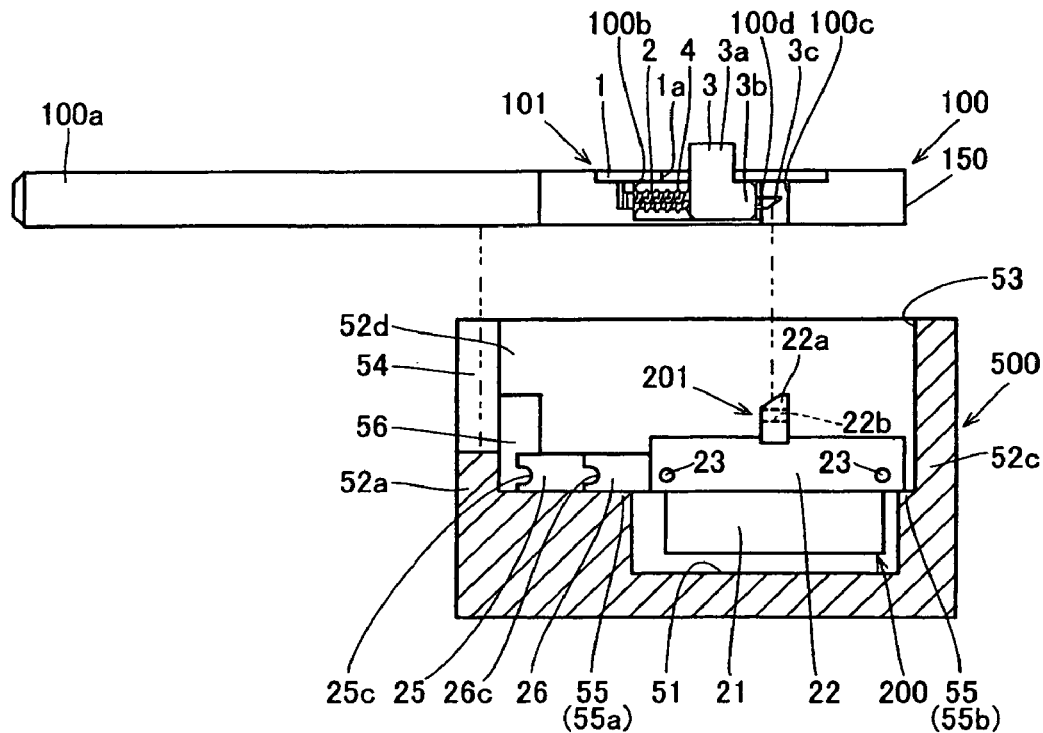
[FIG. 32] A schematic view for illustrating an attaching operation of a head unit to a holder unit of a tissue cutting device according to one embodiment of the present invention.

Next, as shown in FIGS. 31 and 32, the horizontal position of the hole 100c constituting the attachment/detachment mechanism portion 101 of the holding part 150 of the holder unit 100 is brought into coincidence with the horizontal position of the attachment portion 22a constituting the attachment/detachment mechanism portion 201 of the head unit 200, while the horizontal position of the handle 100a of the holder unit 100 is brought into coincidence with the horizontal position of the slit portion 54 of the accommodation housing 500.

Figure 33:
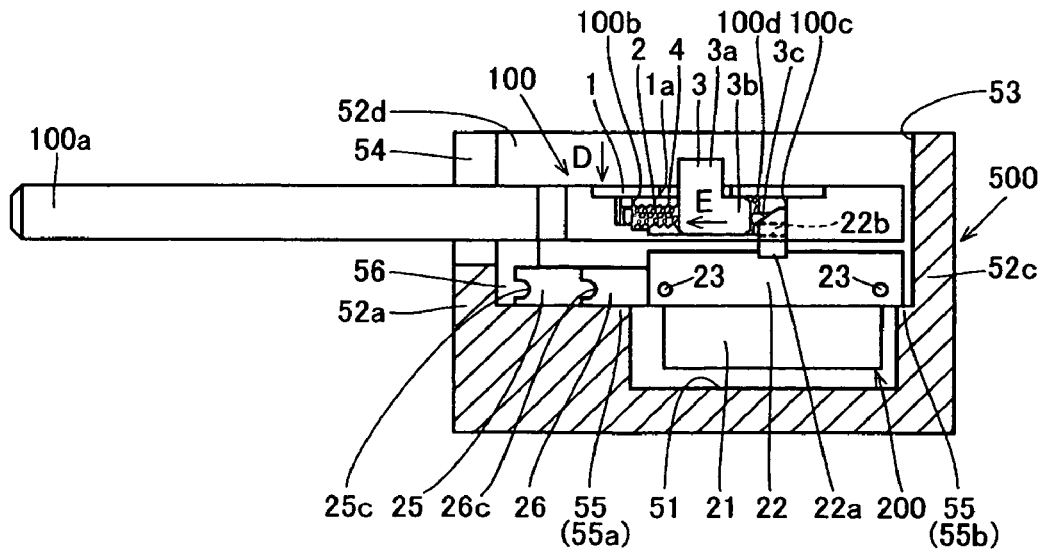
[FIG. 33] A schematic view for illustrating an attaching operation of a head unit to a holder unit of a tissue cutting device according to one embodiment of the present invention.

Then as shown in FIG. 33, in the condition that the horizontal position of the hole 100c and the horizontal position of the attachment portion 22a coincide with each other, and the horizontal positions of the handle 100a and the slit portion 54 coincide with each other, the holder unit 100 is moved downward (in the direction of arrow D). As a result, the holder unit 100 is inserted into the accommodation housing 500, and the attachment portion 22a of the head unit 200 is fitted into the hole 100c of the holding part 150 of the holder unit 100. After the tapered surface at the distal end of the coupler 3c projecting inside the hole 100c comes into contact with the tapered surface of the upper end of the attachment portion 22a, the holder unit 100 is further moved in the direction of the arrow D and thus the movable member 3 is moved in the direction of the arrow E against the biasing force of the compression spring 4.

Figure 34:
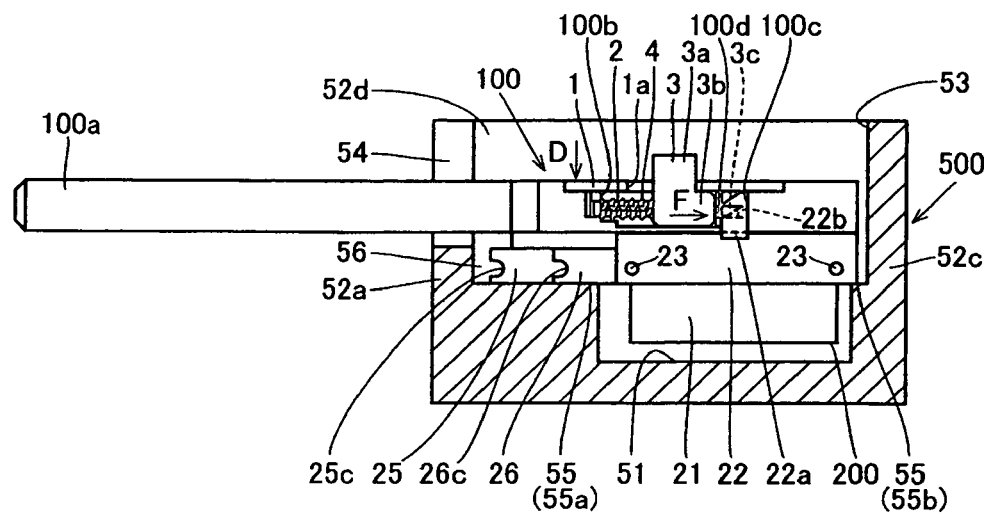
[FIG. 34] A schematic view for illustrating an attaching operation of a head unit to a holder unit of a tissue cutting device according to one embodiment of the present invention.

Then as shown in FIG. 34, the holder unit 100 is further moved in the direction of the arrow D, and vertical positions of the coupler 3c and the engaging hole 22b of the attachment portion 22a are brought into coincidence with each other. As a result, the movable member 3 is moved in the direction of the arrow F by the biasing force of the compression spring 4 so that the coupler 3c comes into engagement with the engaging hole 22b. In this manner, in the present embodiment, it is possible to attach the head unit 200 to the holding part 150 of the holder unit 100 without necessity of an operator's touch to the head unit 200.

Next, as shown in FIG. 35, the mounting member 400 is placed on the pedestal 300. To be more specific, the mounting member 400 is placed on a predetermined position on the base 31 (the region surrounded by the pair of guiding members 32, and the positioning members 34 and 35). At this time, the size of a lymph node 700 (see FIG. 36) is measured with the scale 36, and on which one of the recesses 41a and 41b having different sizes of the mounting member 400 the lymph node 7 should be placed is determined. Then either one of the recesses 41a and 41b on which the lymph node 700 is to be placed is located upstream of the cutting direction (the direction of the arrow C). In the present embodiment, explanation will be made on the case where the lymph node 700 is placed on the recess 41a.

Next, as shown in FIG. 36, the lymph node 700 is placed in the recess 41a located upstream in the cutting direction (direction indicated by the arrow C) of the mounting member 400 by using tweezers. Via the notch 32c of the guiding member 32, adjustment is made so that the center axis of the lymph node 700 placed on the mounting member 400 aligns with the center axial line 41c.

Next, as shown in FIG. 37, on an antislip sheet 800 made of vinyl chloride, the pedestal 300 on which the mounting member 400 is mounted is installed. Thereafter the head unit 200 having the blade 21 attached thereto is inserted between the guiding surfaces 32a of the pair of guiding members 32 from above, and the distal end of the blade edge of the blade 21 is brought into contact with the top face of the positioning member 34. In this case, the vertical position of the end, which is opposite to the distal end of the blade edge of the blade 21, is set to be higher than the top face of the mounting member 400 (urethane sponge member 41).

Next, as shown in FIG. 38, the blade 21 is moved in the direction of the arrow C along the top face of the positioning member 34, to thereby cut the lymph node 700 together with the urethane sponge member 41. Then as shown in FIG. 39, the blade 21 is further moved in the direction of the arrow C along the top face of the supporting member 42. At this time, since the top face of the positioning member 34 is located at higher position than the top face of the supporting member 42, it is possible to prevent the blade 21 from cutting into the supporting member 42 in the boundary between the positioning member 34 and the supporting member 42. In other words, it is possible to prevent the blade 21 from becoming difficult to move in the direction of the arrow C due to the blade 21 cutting into the supporting member 42 as shown in FIG. 40. In this manner, the lymph node 700 is split into four sections having a predetermined thickness (about 2 mm) as shown in FIG. 41.

It should be noted that embodiments disclosed herein are construed as being given for exemplification and no for limitation. The scope of the present invention indicated by the attached claims rather than the above description of embodiment encompasses all modifications within the equivalent meanings and ranges of the attached claims.

For example, in the above embodiment, explanation was made on the case where a lymph node is cut, however, without limiting to this, the present invention may be applied to the case where a biological tissue other than a lymph node is cut. For example, similar effects can be obtained for cutting of a permanent tissue specimen fixed by formalin or the like is cut, or for cutting an excised colon polyp.

In the above embodiment, a biological tissue was split into four sections using three blades, however, in the present invention, a biological tissue may be split into three sections using two blades, or split into four or more sections using four or more blades without limited to the above.

In the above embodiment, the interval of blades was set at about 2 mm using a spacer having a thickness of about 2 mm, however, the interval of blades may be adjusted depending on the size of the biological tissue or purpose of the test without limited to the above. In this case, the interval of blades may be readily adjusted by adjusting the thickness of the spacer.

In the present embodiment, a blade having a thickness of about 0.1 mm was used, however, in the present invention, any blades having a thickness of about 0.5 mm or less may be used without limited to the above. By setting the thickness of the blade at about 0.5 mm, it is possible to prevent occurrence of a trouble that structure of a biological tissue is broken in cutting the biological tissue.

In the present embodiment, a biological tissue is cut by the tissue cutting device while the biological tissue is placed on the tissue cut assisting device, however, in the present invention, not limited to the above, a biological tissue may be cut only by a tissue cutting device without using a tissue cut assisting device.

What is claimed is:

1. A tissue cutting device configured for cutting a biological tissue into a predetermined thickness, the tissue cutting device comprising:
   an elongated handle;
   a head unit comprising a plurality of rectangular blades each having a cutting edge opposite a long side and a blade holding portion that holds the long side of each of the rectangular blades, wherein the rectangular blades are arranged such that the long sides extend substantially parallel to a longitudinal direction of the elongated handle at predetermined intervals and the cutting edges are positioned away from the blade holding portion by a sufficient distance such that the blades cut the biological tissue into the predetermined thickness; and
   a head holding part disjoint from the head unit and located at a distal end of the elongated handle, the head holding unit including a first engaging portion configured to receive a second engaging portion projecting from the blade holding portion perpendicular to the longitudinal direction and on a side of the blade holding portion opposite to the rectangular blades for detachably holding the head unit, such that the cutting edges of the plurality of rectangular blades are positioned directly and entirely below the head holding part and extend substantially parallel to the longitudinal direction when the first engaging portion has received the second engaging portion.

2. The tissue cutting device according to claim 1, wherein the second engaging portion releasably engages the first engaging portion and is disposed on a side opposite to the rectangular blades.

3. The tissue cutting device according to claim 2, wherein the first engaging portion comprises a moveable first engaging member, the second engaging portion comprises a second engaging member comprising an engaging hole, and the head unit is held by the moveable first engaging member inserted into the engaging hole of the second engaging member.

4. The tissue cutting device according to claim 3, wherein the head holding part comprises a movable member that connects to the moveable first engaging member.

5. The tissue cutting device according to claim 4, wherein the head holding part comprises a biasing member for biasing the movable member in a direction in which the moveable first engaging member is inserted into the engaging hole of the second engaging member.

6. The tissue cutting device according to claim 1, wherein the blade holding portion comprises a spacer for defining the predetermined interval of the plurality of rectangular blades.

7. The tissue cutting device according to claim 6, wherein the spacer is provided in the blade holding portion so as to be movable with respect to the rectangular blades.

8. The tissue cutting device according to claim 7, wherein the spacer comprises a plurality of spacers comprising different lengths.

9. The tissue cutting device according to claim 1, wherein opposing sides extend between the long side and the cutting edge of each rectangular blade and each side of the opposing sides of each rectangular blade comprises a notch for fixation.

10. The tissue cutting device according to claim 1, wherein the head holding part comprises a water discharge hole.

11. The tissue cutting device according to claim 1, wherein the first engaging portion includes an engaging opening, and the second engaging portion comprises an engaging member which detachably engages in the engaging opening and is disposed one the side of the blade holding portion opposite to the rectangular blades.

12. A tissue cutting device configured for cutting a biological tissue into a predetermined thickness, the tissue cutting device comprising:
    an elongated handle;
    a head unit comprising a plurality of rectangular blades each having a cutting edge opposite a long side and a blade holding portion that holds the long side of each of the rectangular blades, wherein the rectangular blades are arranged such that the long sides extend substantially parallel to a longitudinal direction of the elongated handle at predetermined intervals and the cutting edges are positioned away from the blade holding portion by a sufficient distance such that blades cut the biological tissue into the predetermined thickness; and
    a head holding part disjoint from the head unit and located at a distal end of the elongated handle, the head holding part including a cavity housing at least one shaft retractable in the longitudinal direction, the cavity configured to receive an engagement member extending from the blade holding portion perpendicular to the longitudinal direction, wherein the engagement member includes an opening for receiving the at least one retractable shaft to thereby detachably hold the head unit, such that the cutting edges of the plurality of rectangular blades are positioned directly below the head holding part and extend substantially parallel to the longitudinal direction when the at least one retractable shaft is received in the opening of the engagement member.

\* \* \* \* \*

UNITED STATES PATENT AND TRADEMARK OFFICE
CERTIFICATE OF CORRECTION

PATENT NO. : 8,065,945 B2
APPLICATION NO. : 11/262098
DATED : November 29, 2011
INVENTOR(S) : Hironori Kobayashi et al.

It is certified that error appears in the above-identified patent and that said Letters Patent is hereby corrected as shown below:

In column 17, claim 11, line 28, before "the side of the blade" replace "one" with --on--.

Signed and Sealed this
Twenty-ninth Day of May, 2012

David J. Kappos
*Director of the United States Patent and Trademark Office*